(12) United States Patent
Pavlovich

(10) Patent No.: US 11,185,540 B2
(45) Date of Patent: Nov. 30, 2021

(54) EXTENDED RELEASE COMPOSITIONS OF OPIOID ANTAGONISTS AND PHOSPHODIESTERASE 5 INHIBITORS

(71) Applicant: Pardon My Scotch, LLC, Santa Rosa, CA (US)

(72) Inventor: Michael Anthony Pavlovich, Newport Beach, CA (US)

(73) Assignee: PARDON MY SCOTCH LLC., Santa Rosa, CA (US)

( * ) Notice: Subject to any disclaimer, the term of this patent is extended or adjusted under 35 U.S.C. 154(b) by 0 days.

(21) Appl. No.: 16/604,506

(22) PCT Filed: Apr. 11, 2018

(86) PCT No.: PCT/US2018/027186
§ 371 (c)(1),
(2) Date: Oct. 10, 2019

(87) PCT Pub. No.: WO2018/191430
PCT Pub. Date: Oct. 18, 2018

(65) Prior Publication Data
US 2020/0237749 A1    Jul. 30, 2020

Related U.S. Application Data

(63) Continuation of application No. 62/612,129, filed on Dec. 29, 2019.

(60) Provisional application No. 62/484,769, filed on Apr. 12, 2017.

(51) Int. Cl.
A61K 31/485    (2006.01)
A61K 9/00    (2006.01)
A61K 31/4985    (2006.01)
A61K 47/12    (2006.01)

(52) U.S. Cl.
CPC .......... *A61K 31/485* (2013.01); *A61K 9/0024* (2013.01); *A61K 31/4985* (2013.01); *A61K 47/12* (2013.01)

(58) Field of Classification Search
None
See application file for complete search history.

(56) References Cited

U.S. PATENT DOCUMENTS

| 6,203,813 B1 | 3/2001 | Gooberman | |
| 2003/0229111 A1* | 12/2003 | Oshiack | A61K 9/2054 514/282 |
| 2015/0250732 A1 | 9/2015 | Dick et al. | |

FOREIGN PATENT DOCUMENTS

| AU | 785372 | 6/2001 | |
| WO | WO 2017/033208 | 3/2017 | |
| WO | WO-2017033208 A2 * | 3/2017 | A61K 9/1617 |

OTHER PUBLICATIONS

Tihonen et al., "Naltrexone Implant for the Treatment of Polydrug Dependence: A Randomized Controlled Trial," Am. J. Psychiatry, vol. 169, No. 5, May 2012, pp. 531-536.
International Search Report and Written Opinion for International (PCT) Patent Application No. PCT/US2018/027186, dated Jul. 23, 2018, 15 pages.

* cited by examiner

*Primary Examiner* — Melissa S Mercier
(74) *Attorney, Agent, or Firm* — Sheridan Ross P.C.

(57) ABSTRACT

Pharmaceutical compositions of one or more opioid antagonists or phosphodiesterase 5 (PDE5) inhibitors are disclosed.

8 Claims, 3 Drawing Sheets

EXTENDED RELEASE COMPOSITIONS OF OPIOID ANTAGONISTS AND PHOSPHODIESTERASE 5 INHIBITORS

CROSS REFERENCE TO RELATED APPLICATIONS

This application is a U.S. 371 Application of International Application PCT/US2018/027186, filed Apr. 11, 2018, which claims the benefit of U.S. Provisional Application No. 62/484,769, filed Apr. 12, 2017, and U.S. Provisional Application No. 62/612,129, filed Dec. 29, 2017, all of which are herein incorporated by reference in their entirety.

TECHNICAL FIELD

Disclosed herein are pharmaceutical compositions suitable for use as extended, sustained and/or controlled release formulations of opioid antagonists or phosphodiesterase 5 inhibitors.

BACKGROUND

Opioid Antagonists

An opioid antagonist, or opioid receptor antagonist, is a ligand or drug that blocks or dampens agonist-mediated responses on one or more of the opioid receptors, rather than provoking a biological response itself. Pharmacologically, an opioid antagonist has affinity for an opioid receptor, but no efficacy, such that binding will disrupt the interaction between an opioid and its receptor and inhibit the function of that opioid at its receptor.

Naloxone and naltrexone are examples of opioid antagonist drugs. Both are examples of competitive antagonists that compete with an opioid substance for binding at a receptor. Both naloxone and naltrexone bind to opioid receptors with higher affinity than the opioid receptor agonists, but neither activates the receptors. In doing so, both drugs effectively block opioid receptors, preventing the receptors from responding to opioids that may otherwise be present.

Naltrexone is prescribed for the treatment of opioid addiction. It also finds use in the treatment of alcohol addiction, amphetamine addiction, and/or other behavioral addictions. It achieves its effects by competing for binding at the opioid receptors, thereby blocking the effects of opioid drugs. Naltrexone therefore does not lead to physical or psychological dependence. Clinical observations have shown that a sustained course of low-dose naltrexone can reverse the altered neurological homeostasis that often results from abuse of opioid drugs. Low-dose naltrexone can be used as a later, or final, step in the treatment of opioid addiction, after the subject has been weaned off of a substitute agonist (methadone, buprenorphine, etc.), or a substance, in order to restore homeostasis and minimize the risk of post-acute withdrawal syndrome.

Clinical studies have shown that naltrexone, when taken orally, is ineffective; it is not statistically superior to placebo or to taking no anti-opioid medication at all, nor is it superior to benzodiazepine or buprenorphine. Because of this, there is insufficient evidence to support the oral administration of naltrexone to treat opioid use disorders. Even for those rare subjects who respond well to an oral naltrexone formulation, it must be taken daily. This can be particularly problematic, because a subject experiencing overwhelming cravings can obtain opioid intoxication and relapse simply by skipping a dose of the oral formulation. As a result, the use of oral naltrexone is limited by low retention in treatment.

Other forms of naltrexone are available. For example, extended-release depot injections of naltrexone, administered once every 21 to 28 days or once per month, can be effective to treat opioid use disorders. However, such injections are typically administered intramuscularly, leaving large deposits (or depots). These injections may be absorbed and wear off before the next scheduled injection, causing some patients to return to using opiates.

Other opiate antagonist implants are also available, for example the subcutaneous implants described in U.S. Pat. No. 6,203,813 to Gooberman. However, the disclosed implants are still quite large, at least 13 mm in diameter. They can therefore be painful to implant and unattractive for those subjects who receive them, as they are readily visible beneath a subject's skin.

Phosphodiesterase 5 (PDE5) Inhibitors

Phosphodiesterase 5 (PDE5) inhibitors are drugs that block the degradative action of cGMP-specific PDE5 on cyclic GMP in smooth muscle cells, leading to smooth muscle relaxation and increased blood flow. Such smooth muscle cells line the blood vessels supplying the corpus cavernosum of the penis. Thus, when present during sexual stimulation, PDE5 inhibitors can cause an increase in blood flow and erection. In a similar manner, PDE5 inhibitors can also influence the smooth muscle cells which line the blood vessels of the arterial wall of the lungs.

Examples of commonly used PDE5 inhibitors include tadalafil, vardenafil, sildenafil, avanafil, lodenafil, mirodenafil, udenafil, zaprinast, Icariin, benzamidenafil, and dasantafil.

PDE5 inhibitors are prescribed in oral form for treating erectile dysfunction. PDE5 inhibitors are also prescribed in oral form for treating pulmonary hypertension, benign prostatic hyperplasia or a combination of erectile dysfunction and benign prostatic hyperplasia. PDE5 inhibitors, for use in treatment of the aforementioned conditions, are also available in injectable form. The relatively short duration of action of PDE5 inhibitors when administered by injection, however, limits the utility of this mode of delivery to acute care settings. There is, therefore, a need for a superior route of delivery of PDE5 inhibitors, particularly in a manner capable of maintaining a consistent dose level of PDE5 inhibitors over an extended period of time.

SUMMARY

Therefore, alternative forms of administering opioid antagonists for the treatment of, for example, opioid use disorders, are desired. Further, alternative forms for administering PDE5 inhibitors for the treatment of, for example, erectile dysfunction, are also desired. Disclosed herein are subcutaneously implantable pellet formulations of pharmaceutical compositions comprising opioid antagonists or PDE5 inhibitors.

PDE5 inhibitors are not currently available in pellet or implantable form, therefore the disclosed PDE5 formulations are completely new. The disclosed opioid antagonist formulations are significantly smaller than known implantable pellet opioid antagonist formulations and thus greatly improve, and in some instances completely overcome, the limitations of known pellet formulations, namely excessive pain experienced by a subject and subject non-compliance. The disclosed pellet formulations of both opioid antagonists and PDE5 inhibitors also improve the limitations of known oral formulations for these drugs, namely reducing the need for patient compliance in remembering to take an oral pill. Further, the disclosed pellet formulations are able to supply a consistent drug level to a subject over an extended period of time and thus reduce the likelihood of experiencing adverse events associated with spikes in blood concentration of an active pharmaceutical ingredient.

In various aspects, the present disclosure provides pharmaceutical compositions of opioid antagonists or PDE5 inhibitors that are subcutaneously implantable. The disclosed compositions are capable of delivering an extended release of the opioid antagonists or PDE5 inhibitors to a subject over a period of days, weeks and/or months. The disclosed compositions are substantially smaller than known pellet compositions and will thus advantageously improve compliance with use, due to decreased pain and post-implantation visibility. Because they are implanted subcutaneously, the disclosed compositions also overcome the deficiencies associated with oral administration of opioid antagonists or PDE5 inhibitors.

In one aspect, subcutaneously implantable pharmaceutical compositions are provided, comprising: one or more opioid antagonists, a pharmaceutically acceptable lubricant, a pharmaceutically acceptable vehicle, an antioxidant and/or ascorbic acid.

In another aspect, subcutaneously implantable pharmaceutical compositions are provided, comprising: one or more PDE5 inhibitors, a pharmaceutically acceptable lubricant, a pharmaceutically acceptable vehicle, an antioxidant and/or ascorbic acid.

The opioid antagonist compositions and dosage forms disclosed herein can be used to treat any number of diseases for which opioid antagonists are known or thought to be therapeutically effective. In several aspects, the opioid antagonist-containing compositions disclosed herein comprise naltrexone and are useful for treating alcohol addiction. In several aspects, the opioid antagonist-containing compositions disclosed herein comprise naltrexone and are useful for treating opioid drug addiction. In several aspects, the opioid antagonist-containing compositions disclosed herein comprise naltrexone and are useful for treating amphetamine addiction. In several aspects, the opioid antagonist-containing compositions disclosed herein comprise naltrexone and are useful for treating sex addiction, pathological gambling, and/or other behavioral addictions.

The PDE5 inhibitor compositions and dosage forms disclosed herein can be used to treat any number of diseases for which PDE5 inhibitors are known or thought to be therapeutically effective. In several aspects, the PDE5 inhibitor-containing compositions disclosed herein comprise tadalafil and are useful for treating erectile dysfunction. In several aspects, the PDE5 inhibitor-containing compositions disclosed herein comprise tadalafil and are useful for treating pulmonary hypertension. In several aspects, the PDE5 inhibitor-containing compositions disclosed herein comprise tadalafil and are useful for treating benign prostatic hyperplasia. In several aspects, the PDE5 inhibitor-containing compositions disclosed herein comprise tadalafil and are useful for treating erectile dysfunction in combination with benign prostatic hyperplasia.

FIGURES

FIGS. 1A, 1B, and 1C show three views of an example of a blister pack suitable for sterilizing, storing and/or transporting a pellet, according to some embodiments.

DEFINITIONS

Figure 1A:

"Opioid antagonist" refers to a ligand or drug that blocks or dampens agonist-mediated responses on one or more of the opioid receptors, rather than provoking a biological response itself. Such antagonists include naloxone, naltrexone including the base form of naltrexone, nalmefene, diprenorphine, nalorphine, nalorphine dinicotinate, levallorphan, samidorphan, nalodeine, alvimopan, methylnaltrexone, naloxegol, 6β-naltrexol, axelopran, bevenopran, methylsamidorphan, naldemedine, buprenorphine, dezocine, eptazocine, butorphanol, levorphanol, nalbuphine, pentazocine, and phenazocine.

"PDE5 inhibitor" refers to a drug or drugs that block or dampen the degradative action of cGMP-specific phosphodiesterase 5 (PDE5) on cyclic GMP. Such drugs include tadalafil, vardenafil, sildenafil, avanafil, lodenafil, mirodenafil, udenafil, zaprinast, Icariin, benzamidenafil, and dasantafil.

"Pharmaceutically acceptable" refers to approved or approvable by a regulatory agency of a government, such as the U.S. FDA or the EMA, or listed in the U.S. Pharmacopoeia or other generally recognized pharmacopoeia for use in mammals and/or animals, and more particularly in humans.

"Subject" refers to a mammal, for example, a human.

"Treat," "treating" or "treatment" of any disease refers to reversing, alleviating, arresting, or ameliorating a disease or at least one of the clinical symptoms of a disease or inhibiting the progress of a disease or at least one of the clinical symptoms of the disease. "Treat," "treating" or "treatment" also refers to inhibiting the disease, either physically, (e.g., stabilization of a discernible symptom), physiologically, (e.g., stabilization of a physical parameter), or both, and to inhibiting at least one physical parameter that may or may not be discernible to the subject.

"Therapeutically effective amount" refers to the amount of an opioid antagonist or PDE5 inhibitor that, when administered to a subject for treating a disease, or at least one of the clinical symptoms of a disease, is sufficient to affect such treatment of the disease or symptom thereof. The "therapeutically effective amount" may vary depending, for example, on the opioid antagonist or PDE5 inhibitor, the disease and/or symptoms of the disease, severity of the disease and/or symptoms of the disease or disorder, the age, weight, and/or health of the subject to be treated, and the judgment of the prescribing physician.

"Therapeutically effective dose" refers to a dose that provides effective treatment of a disease or disorder in a subject. A therapeutically effective dose may vary from compound to compound, and from subject to subject, and may depend upon factors such as the condition of the subject, genetic character of the subject, and the route of delivery.

DETAILED DESCRIPTION

Medical professionals worldwide rely on opioid antagonists to treat a variety of indications including, without limitation, opioid drug, amphetamine, and/or alcohol addiction. Additionally, such professionals are mindful of the desire a subject will have to maintain a regular lifestyle, and thus prefer to utilize extended release formulations, particularly those that are subcutaneously implanted, removing the need for a subject to remember to take a daily pill. Implants that are small in size, therefore less likely to draw the attention of others, are further valued. Hence there exists a need for extended release compositions of opioid antagonists that provide therapeutically effective doses of opioid antagonists over an extended period of time, and that are smaller in size than those known in the art.

Likewise, medical professionals worldwide rely on PDE5 inhibitors to treat a variety of indications including, without limitation, erectile dysfunction, pulmonary arterial hypertension, benign prostatic hyperplasia and erectile dysfunction in combination with benign prostatic hyperplasia. Additionally, such professionals are mindful of the desire a subject will have to maintain a regular lifestyle, and thus prefer to utilize extended release formulations, particularly those that are subcutaneously implanted, removing the need for a subject to remember to take a daily pill. An added benefit of extended release formulations is that their delivery avoids a subject's mental connection between the processes of taking a medication with a sexual encounter. Implants that are small in size, therefore less likely to draw the attention of others, are further valued. Hence there exists a need for implantable extended release compositions of PDE5 inhibitors.

Pharmaceutical Compositions

Pharmaceutical compositions provided by the present disclosure may comprise a therapeutically effective amount of one or more opioid antagonists or one or more PDE5 inhibitors, together with a suitable amount of one or more pharmaceutically acceptable vehicles and/or lubricants, so as to provide a composition for proper administration to a subject.

Pharmaceutical compositions provided by the present disclosure may be formulated in a unit dosage form. A unit dosage form refers to a physically discrete unit suitable as a unitary dose for subjects undergoing treatment, with each unit containing a predetermined quantity of the opioid antagonist(s) or a predetermined quantity of the PDE5 inhibitor(s) calculated to produce an intended therapeutic effect. In various aspects, a unit dosage form is a pellet suitable for subcutaneous implantation. A unit dosage form may be for a single dose, for administration 2 or more times per year, or one of multiple doses, e.g., 2 or more unit dosage forms administered at a single time. When multiple dosage forms are administered at a single time, each unit dosage form may contain the same amount of opioid antagonist(s) or PDE5 inhibitor(s) or each dosage form may contain different amounts. A unit dosage form may also be formulated on the basis of the metabolism of the subject.

The pharmaceutical compositions provided by the present disclosure are extended release compositions. In that respect, extended release means that the disclosed compositions are formulated so that they release one or more opioid antagonist(s) or PDE5 inhibitor(s) slowly, over a period of time. This has the advantage of requiring administration of the compositions less often and may also minimize side effects of the opioid antagonist(s) or PDE5 inhibitor(s) as the amount of the drug administered to the subject is consistent over a period of time.

The extended release provided by the disclosed pharmaceutical compositions may be: a) sustained release, where opioid antagonist(s) or PDE5 inhibitor(s) are released over a sustained period of time but not at a constant rate; orb) controlled release, where opioid antagonist(s) or PDE5 inhibitor(s) are released over a sustained period of time and at a constant rate. The disclosed compositions can be designed to deliver one or more opioid antagonists or PDE5 inhibitor(s) in such a way that the level of the drug(s) is maintained within a therapeutically effective window, and such that safe and effective blood levels are maintained for a period as long as the pharmaceutical compositions continue to deliver the drug(s) with a particular release profile. Extended release opioid antagonist or PDE5 inhibitor delivery may produce substantially constant blood levels of drugs over a period of time, as compared to fluctuations observed with immediate release dosage forms. For some applications, maintaining a constant blood and tissue concentration throughout the course of therapy is the most desirable mode of treatment. Immediate release of drug may cause blood levels to peak above the level required to elicit a desired response, which may waste the drug and may cause or exacerbate toxic side effects. Additionally, administration of immediate release formulations requires a large degree of compliance from a subject, for example in the form of taking a dosage form one or more times per day, or every other day. The use of such dosage forms can be problematic for those subjects who do not take the dosage form regularly or who do not desire to take the dosage form at all, in which case the therapeutic effect of the drug will be minimized. Extended release of opioid antagonist(s) or PDE5 inhibitor(s) can result in optimum therapy, and not only can reduce the frequency of dosing, but may also reduce the severity of side effects.

The disclosed pharmaceutical compositions can deliver one or more opioid antagonist(s) or PDE5 inhibitor(s) to a subject over a prolonged period of time. In that respect, the disclosed pharmaceutical compositions are formulated to slowly erode over a period of time after administration. In various aspects, the disclosed pharmaceutical compositions are formulated for subcutaneous administration/implantation. Upon implantation, the compositions begin to erode slowly, over a period of time, thereby delivering a consistent dose of the opioid antagonist(s) or PDE5 inhibitor(s) to the subject, until such time as the composition has completely eroded. The manner in which the compositions are generated causes the opioid antagonist(s) or PDE5 inhibitor(s) to be uniformly dispersed throughout the entirety of the compositions, thereby ensuring that the amount of opioid antagonist(s) or PDE5 inhibitor(s) released is directly proportional to the rate of erosion of the composition. This ensures that the amount of opioid antagonist(s) or PDE5 inhibitor(s) delivered to the subject is consistent for the entire time the composition is present in the subject's body. In various aspects, the disclosed compositions are cylindrically shaped, in order to take advantage of the larger surface area exposed to blood flow after implantation. A spherical-shaped pellet will have the smallest surface area per weight, which will lead to a slower dissolution rate.

In some aspects, to achieve the desired therapeutic range of opioid antagonist(s) or PDE5 inhibitor(s), multiple pellets may be utilized at one time in a single subject.

In various embodiments, the amount of time in which the disclosed pharmaceutical compositions may deliver one or more opioid antagonist(s) or PDE5 inhibitor(s) to a subject can range from 60 days-10 months, in some embodiments from 90 days-9 months.

In one aspect, a pharmaceutical composition is provided which comprises: (a) a therapeutically effective amount of one or more opioid antagonists; (b) one or more pharmaceutically acceptable lubricants; (c) one or more pharmaceutically acceptable vehicles; and, optionally, (d) one or more antioxidants.

The present inventor has surprisingly discovered that the use of ascorbic acid in the disclosed compositions unexpectedly provides stability to the compositions, independent of its antioxidant properties. In this stabilizing capacity, ascorbic acid appears to assume the role of a vehicle (a binder and/or filler). For example, during development of some embodiments of the disclosed compositions, formulations were generated that removed the binder (e.g., removal of povidone K-30). Without a binder in the formulation, the resulting pellets easily crumbled, making them commercially inviable. Glyceryl monostearate (GMS) was then included into such formulations, however GMS, which is the glycerol ester of stearic acid, functions more like a lubricant than a binder. The presence of GMS, by itself, rendered an even "crumblier" pellet, showing that GMS was not functioning as a binder, nor was it improving the commercial viability of the compositions. Adding ascorbic acid to such formulations, without adding any other "true" binder, unexpectedly solved that problem. The resulting pellets no longer crumbled; they were structurally intact and capable of forming commercially viable pellets. This was surprising, as it was not at all expected that ascorbic acid, known for its antioxidant properties, would or could play the role of a binder in a formulation, much in the way povidone does, in addition to providing antioxidant properties. Therefore, in the disclosed pharmaceutical compositions, ascorbic acid can be used as both a pharmaceutically acceptable vehicle and an antioxidant. Another advantage of using ascorbic acid instead of a typical vehicle is that some subjects are sensitive to such vehicles (such as povidone) and can experience a local inflammatory reaction at the implant site. A similar sensitivity has not been seen for ascorbic acid. The amount of ascorbic acid contained in an entire pellet, according to the disclosed compositions, is less than the recommended daily allowance of ascorbic acid.

Thus, in some aspects the pharmaceutical composition comprises: (a) a therapeutically effective amount of one or more opioid antagonists; (b) one or more pharmaceutically acceptable lubricants; and (c) ascorbic acid. The composition may further optionally comprise one or more additional pharmaceutically acceptable vehicles; and/or one or more antioxidants.

In another aspect, a pharmaceutical composition is provided which comprises: (a) a therapeutically effective amount of one or more PDE5 inhibitors; (b) one or more pharmaceutically acceptable lubricants; (c) one or more pharmaceutically acceptable vehicles; and, optionally, (d) one or more antioxidants.

In some aspects, the pharmaceutical composition comprises: (a) a therapeutically effective amount of one or more PDE5 inhibitors; (b) one or more pharmaceutically acceptable lubricants; and (c) ascorbic acid. The composition may further, optionally comprise one or more additional pharmaceutically acceptable vehicles; and/or one or more antioxidants.

In some embodiments, the opioid antagonist(s) or PDE5 inhibitor(s) is/are in a crystalline form. In some embodiments, the opioid antagonist(s) or PDE5 inhibitor(s) is/are amorphous.

The pharmaceutically acceptable lubricant(s) prevent the components of the pharmaceutical composition from clumping together and from sticking to the pellet press that generates the disclosed compositions. The lubricant(s) also ensure that the formation of the pellet, as well as its ejection from the pellet press, occurs with low friction between the composition and the wall of the pellet press. In some embodiments, the lubricant(s) are added to a pharmaceutical composition in order to improve processing characteristics, for example to help increase the flexibility of the compositions, thereby reducing breakage.

The type of lubricant that may be used in the disclosed pharmaceutical compositions can vary. In some embodiments, the pharmaceutically acceptable lubricant is selected from talc, silica, vegetable stearin, magnesium stearate, stearic acid, calcium stearate, glyceryl monostearate (GMS) or glyceryl monostearate salts, glyceryl behenate, glyceryl palmitostearate, mineral oil, polyethylene glycol, sodium stearyl fumarate, sodium lauryl sulfate, vegetable oil, zinc stearate, and combinations thereof. In some embodiments, the pharmaceutically acceptable lubricant is stearic acid. In some embodiments, the pharmaceutically acceptable lubricant is glyceryl monostearate or glyceryl monostearate salts.

The type of vehicles that may be used in the disclosed pharmaceutical compositions can vary. In some embodiments, the pharmaceutically acceptable vehicles are selected from binders, fillers and combinations thereof. In some embodiments, the pharmaceutically acceptable vehicle is selected from ascorbic acid, polyvinylpyrrolidone, polyvinylpyrrolidone K-30 (povidone K-30), glyceryl monostearate (GMS) or glyceryl monostearate salts, glyceryl behenate, glyceryl palmitostearate, hydroxypropyl cellulose, hydroxypropyl methylcellulose, methylcellulose, hydroxyethyl cellulose, sugars, dextran, cornstarch, dibasic calcium phosphate, dibasic calcium phosphate dihydrate, calcium sulfate, dicalcium phosphate, tricalcium phosphate, lactose, cellulose including microcrystalline cellulose, mannitol, sodium chloride, dry starch, pregelatinized starch, compressible sugar, mannitol, lactose monohydrate, starch, dibasic calcium phosphate dihydrate, calcium sulfate, dicalcium phosphate, tricalcium phosphate, powdered cellulose, microcrystalline cellulose, lactose, glucose, fructose, sucrose, mannose, dextrose, galactose, the corresponding sugar alcohols and other sugar alcohols, such as mannitol, sorbitol, xylitol, and combinations of any of the foregoing. In some embodiments, the pharmaceutically acceptable vehicle is polyvinylpyrrolidone K-30, also known as povidone K-30. In some embodiments, the pharmaceutically acceptable vehicle is polyvinylpyrrolidone K-30, also known as povidone K-30, having an average molecular weight of MW of 40,000 (CAS 9003-39-8). In some embodiments, the pharmaceutically acceptable vehicle is selected from glyceryl monostearate (GMS) or glyceryl monostearate salts, glyceryl behenate and glyceryl palmitostearate. In some embodiments, the pharmaceutically acceptable vehicle is glyceryl monostearate (GMS) or glyceryl monostearate salts. In some embodiments, the pharmaceutically acceptable vehicle is glyceryl behenate. In some embodiments, the pharmaceutically acceptable vehicle is glyceryl palmitostearate. In some embodiments, the pharmaceutically acceptable vehicle is ascorbic acid.

In some embodiments, the antioxidants prevent oxidation of the other components of the disclosed compositions. Oxidation can occur, for example, during sterilization where free radicals are generated. Addition of the antioxidants, or free radical scavengers, significantly reduces oxidation and makes the composition more pharmaceutically acceptable for use in subjects.

The type of antioxidants that may be used in the disclosed pharmaceutical compositions can vary. In some embodiments, the antioxidant is selected from methyl paraben and salts thereof, propyl paraben and salts thereof, vitamin E, vitamin E TPGS, propyl gallate, sulfites, ascorbic acid (aka L-ascorbic acid, also including the L-enantiomer of ascorbic acid, vitamin C), sodium benzoate, citric acid, cyclodextrins, peroxide scavengers, benzoic acid, ethylenediaminetetraacetic acid (EDTA) and salts thereof, chain terminators (e.g., thiols and phenols), butylated hydroxytoluene (BHT), butylated hydroxyanisole (BHA), and combinations thereof.

As noted throughout the present disclosure, the disclosed pellets can comprise either one or more opioid antagonists, or one or more PDE5 inhibitors as active pharmaceutical ingredients.

In one aspect, the disclosed pellet compositions comprise one or more opioid antagonists.

The amount of the opioid antagonist in the composition can vary. In some embodiments, the amount of opioid antagonist ranges from 1 mg-2,000 mg, in some embodiments from 200 mg-2000 mg, in some embodiments from 200 mg-1,200 mg, in some embodiments from 200 mg-800 mg, and in some embodiments from 200 mg-600 mg.

In a first embodiment of a composition comprising opioid antagonist(s), a pharmaceutical composition is provided, comprising: (a) one or more opioid antagonists in an amount selected from 70.0-95.0% and 80.0-90.0% of the composition; (b) one or more pharmaceutically acceptable lubricants in an amount selected from 6.0-15.0% and 10.0-13.0% of the composition; (c) one or more pharmaceutically acceptable vehicles in an amount ranging from 2.0-6.0% of the composition; and (d) ascorbic acid in an amount of ≤1% of the composition.

In a second embodiment of a composition comprising opioid antagonist(s), a pharmaceutical composition is provided, comprising: (a) naltrexone in an amount ranging from 82.6-87.0% of the composition; (b) stearic acid in an amount ranging from 10.4-12.5% of the composition; (c) povidone K-30 in an amount ranging from 2.3-4.8% of the composition; and (d) ascorbic acid in an amount of 0.2% of the composition. In some embodiments, the povidone K-30 has an average molecular weight of 40,000 (CAS 9003-39-8).

In a third embodiment of a composition comprising opioid antagonist(s), a pharmaceutical composition is provided, comprising: (a) naltrexone in an amount of 87.0% of the composition; (b) stearic acid in an amount ranging from 10.4-10.6% of the composition; (c) povidone K-30 in an amount ranging from 2.3-2.5% of the composition; and (d) ascorbic acid in an amount of 0.2% of the composition. In some embodiments, the povidone K-30 has an average molecular weight of 40,000 (CAS 9003-39-8).

In a fourth embodiment of a composition comprising opioid antagonist(s), a pharmaceutical composition is provided, comprising: (a) naltrexone in an amount of 82.6% of the composition; (b) stearic acid in an amount ranging from 12.3-12.5% of the composition; (c) povidone K-30 in an amount ranging from 4.6-4.8% of the composition; and (d) ascorbic acid in an amount of 0.2% of the composition. In some embodiments, the povidone K-30 has an average molecular weight of 40,000 (CAS 9003-39-8).

In a fifth embodiment of a composition comprising opioid antagonist(s), a pharmaceutical composition is provided, comprising: (a) naltrexone in an amount ranging from 76.8-86.8% of the composition; (b) stearic acid in an amount of 6% of the composition; (c) glyceryl monostearate (GMS) or glyceryl monostearate salts, in an amount ranging from 10-20% of the composition; and (d) ascorbic acid in an amount of 0.2% of the composition.

In a sixth embodiment of a composition comprising opioid antagonist(s), a pharmaceutical composition is provided, comprising: (a) naltrexone in an amount of 86.8% of the composition; (b) stearic acid in an amount of 6% of the composition; (c) glyceryl monostearate (GMS) or glyceryl monostearate salts, in an amount of 10% of the composition; and (d) ascorbic acid in an amount of 0.2% of the composition.

In a seventh embodiment of a composition comprising opioid antagonist(s), a pharmaceutical composition is provided, comprising: (a) naltrexone in an amount of 76.8% of the composition; (b) stearic acid in an amount of 6% of the composition; (c) glyceryl monostearate (GMS) or glyceryl monostearate salts, in an amount of 20% of the composition; and (d) ascorbic acid in an amount of 0.2% of the composition.

In an eighth embodiment of a composition comprising opioid antagonist(s), a pharmaceutical composition is provided, comprising: (a) naltrexone in an amount ranging from 76.8-86.8% of the composition; (b) stearic acid in an amount of 6% of the composition; (c) glyceryl behenate in an amount ranging from 10-20% of the composition; and (d) ascorbic acid in an amount of 0.2% of the composition.

In a ninth embodiment of a composition comprising opioid antagonist(s), a pharmaceutical composition is provided, comprising: (a) naltrexone in an amount of 86.8% of the composition; (b) stearic acid in an amount of 6% of the composition; (c) glyceryl behenate in an amount of 10% of the composition; and (d) ascorbic acid in an amount of 0.2% of the composition.

In a tenth embodiment of a composition comprising opioid antagonist(s), a pharmaceutical composition is provided, comprising: (a) naltrexone in an amount of 76.8% of the composition; (b) stearic acid in an amount of 6% of the composition; (c) glyceryl behenate in an amount of 20% of the composition; and (d) ascorbic acid in an amount of 0.2% of the composition.

In an eleventh embodiment of a composition comprising opioid antagonist(s), a pharmaceutical composition is provided, comprising: (a) naltrexone in an amount ranging from 76.8-86.8% of the composition; (b) stearic acid in an amount of 6% of the composition; (c) glyceryl palmitostearate, in an amount ranging from 10-20% of the composition; and (d) ascorbic acid in an amount of 0.2% of the composition.

In a twelfth embodiment of a composition comprising opioid antagonist(s), a pharmaceutical composition is provided, comprising: (a) naltrexone in an amount of 86.8% of the composition; (b) stearic acid in an amount of 6% of the composition; (c) glyceryl palmitostearate in an amount of 10% of the composition; and (d) ascorbic acid in an amount of 0.2% of the composition.

In a thirteenth embodiment of a composition comprising opioid antagonist(s), a pharmaceutical composition is provided, comprising: (a) naltrexone in an amount of 76.8% of the composition; (b) stearic acid in an amount of 6% of the composition; (c) glyceryl palmitostearate in an amount of 20% of the composition; and (d) ascorbic acid in an amount of 0.2% of the composition.

In a fourteenth embodiment of a composition comprising opioid antagonist(s), a pharmaceutical composition is provided, comprising: (a) one or more opioid antagonists in an amount ranging from 70.0-95.0% of the composition; (b) one or more pharmaceutically acceptable lubricants in an amount ranging from 6.0-15.0% of the composition; and (c) ascorbic acid in an amount of 0.2% of the composition.

In some embodiments, the composition comprises: (a) one or more opioid antagonists in an amount ranging from 80.0-90.0% of the composition; (b) one or more pharmaceutically acceptable lubricants in an amount ranging from 10.0-13.0% of the composition; and (c) ascorbic acid in an amount of 0.2% of the composition.

In some embodiments, the composition comprises: (a) one or more opioid antagonists in an amount ranging from 82.6-87.0% of the composition; (b) one or more pharmaceutically acceptable lubricants in an amount ranging from 10.5-12.4% of the composition; and (c) ascorbic acid in an amount of 0.2% of the composition.

In some embodiments, a pharmaceutical composition is provided, which comprises: (a) naltrexone in an amount of 86.8% of the composition; (b) stearic acid in an amount of 6% of the composition; and (c) ascorbic acid in an amount of 0.2% of the composition.

In some embodiments, the composition comprises: (a) naltrexone in an amount of 76.8% of the composition; (b) stearic acid in an amount of 6% of the composition; and (c) ascorbic acid in an amount of 0.2% of the composition.

In some embodiments, the composition further comprises one or more pharmaceutically acceptable vehicles in an amount ranging from 2.0-6.0% of the composition; and/or one or more antioxidants in an amount of ≤1% of the composition.

The amount of naltrexone in the compositions can vary. In some embodiments, the amount of naltrexone in a composition ranges from 200 mg-2,000 mg, in some embodiments from 200 mg-1,200 mg, in some embodiments from 200 mg-800 mg, and in some embodiments from 200 mg-600 mg. In some embodiments, the amount of naltrexone in a composition is selected from 200 mg, 600 mg, 800 mg, 1200 mg and 2000 mg. In some embodiments, the amount of naltrexone in a composition is 200 mg. In some embodiments, the amount of naltrexone in a composition is 600 mg. In some embodiments, the amount of naltrexone in a composition is 800 mg. In some embodiments, the amount of naltrexone in a composition is 1,200 mg. In some embodiments, the amount of naltrexone in a composition is 2,000 mg.

In some embodiments, the amount of naltrexone in the composition is 200 mg and the composition is formulated to slowly erode upon administration to a subject over a period of 80-100 days, in some embodiments over a period of 90 days.

In some embodiments, the amount of naltrexone in the composition is 600 mg and the composition is formulated to slowly erode upon administration to a subject over a period of 5-7 months, in some embodiments over a period of 6 months.

In some embodiments, the amount of naltrexone in the composition is 800 mg and the composition is formulated to slowly erode upon administration to a subject over a period of 5-7 months, in some embodiments over a period of 6 months.

In some embodiments, the amount of naltrexone in the composition is 1200 mg and the composition is formulated to slowly erode upon administration to a subject over a period of up to 9 months.

In another aspect, the disclosed pellet compositions comprise one or more PDE5 inhibitors.

The amount of PDE5 inhibitor in the compositions can vary. In some embodiments of a composition comprising PDE5 inhibitors, the amount of PDE5 inhibitor ranges from 25 mg-2,000 mg, in some embodiments from 25 mg-100 mg, in some embodiments from 100 mg-200 mg, 200 mg-1,200 mg, in some embodiments from 200 mg-800 mg, in some embodiments from 1,200 mg-2,000 mg, and in some embodiments from 200 mg-600 mg.

In some embodiments, the amount of PDE5 inhibitor in the composition is 100 mg and the composition is formulated to slowly erode upon administration to a subject over a period of 80-100 days, in some embodiments over a period of 90 days.

In a first embodiment of a composition comprising PDE5 inhibitor(s), a pharmaceutical composition is provided, comprising: (a) one or more PDE5 inhibitors in an amount selected from 70.0-95.0% and 80.0-90.0% of the composition; (b) one or more pharmaceutically acceptable lubricants in an amount selected from 6.0-15.0% and 10.0-13.0% of the composition; (c) one or more pharmaceutically acceptable vehicles in an amount ranging from 2.0-6.0% of the composition; and (d) ascorbic acid in an amount of ≤1% of the composition.

In a second embodiment of a composition comprising PDE5 inhibitor(s), a pharmaceutical composition is provided, comprising: (a) tadalafil in an amount ranging from 82.6-87.0% of the composition; (b) stearic acid in an amount ranging from 10.4-12.5% of the composition; (c) povidone K-30 in an amount ranging from 2.3-4.8% of the composition; and (d) ascorbic acid in an amount of 0.2% of the composition. In some embodiments, the povidone K-30 has an average molecular weight of 40,000 (CAS 9003-39-8).

In a third embodiment of a composition comprising PDE5 inhibitor(s), a pharmaceutical composition is provided, comprising: (a) tadalafil in an amount of 87.0% of the composition; (b) stearic acid in an amount ranging from 10.4-10.6% of the composition; (c) povidone K-30 in an amount ranging from 2.3-2.5% of the composition; and (d) ascorbic acid in an amount of 0.2% of the composition. In some embodiments, the povidone K-30 has an average molecular weight of 40,000 (CAS 9003-39-8).

In a fourth embodiment of a composition comprising PDE5 inhibitor(s), a pharmaceutical composition is provided, comprising: (a) tadalafil in an amount of 82.6% of the composition; (b) stearic acid in an amount ranging from 12.3-12.5% of the composition; (c) povidone K-30 in an amount ranging from 4.6-4.8% of the composition; and (d) ascorbic acid in an amount of 0.2% of the composition. In some embodiments, the povidone K-30 has an average molecular weight of 40,000 (CAS 9003-39-8).

In a fifth embodiment of a composition comprising PDE5 inhibitor(s), a pharmaceutical composition is provided, comprising: (a) tadalafil in an amount ranging from 76.8-86.8% of the composition; (b) stearic acid in an amount of 6% of the composition; (c) glyceryl monostearate (GMS) or glyceryl monostearate salts, in an amount ranging from 10-20% of the composition; and (d) ascorbic acid in an amount of 0.2% of the composition.

In a sixth embodiment of a composition comprising PDE5 inhibitor(s), a pharmaceutical composition is provided, comprising: (a) tadalafil in an amount of 86.8% of the composition; (b) stearic acid in an amount of 6% of the composition; (c) glyceryl monostearate (GMS) or glyceryl monostearate salts, in an amount of 10% of the composition; and (d) ascorbic acid in an amount of 0.2% of the composition.

In a seventh embodiment of a composition comprising PDE5 inhibitor(s), a pharmaceutical composition is provided, comprising: (a) tadalafil in an amount of 76.8% of the composition; (b) stearic acid in an amount of 6% of the composition; (c) glyceryl monostearate (GMS) or glyceryl monostearate salts, in an amount of 20% of the composition; and (d) ascorbic acid in an amount of 0.2% of the composition.

In an eighth embodiment of a composition comprising PDE5 inhibitor(s), a pharmaceutical composition is provided, comprising: (a) tadalafil in an amount ranging from 76.8-86.8% of the composition; (b) stearic acid in an amount of 6% of the composition; (c) glyceryl behenate in an amount ranging from 10-20% of the composition; and (d) ascorbic acid in an amount of 0.2% of the composition.

In a ninth embodiment of a composition comprising PDE5 inhibitor(s), a pharmaceutical composition is provided, comprising: (a) tadalafil in an amount of 86.8% of the composition; (b) stearic acid in an amount of 6% of the composition; (c) glyceryl behenate in an amount of 10% of the composition; and (d) ascorbic acid in an amount of 0.2% of the composition.

In a tenth embodiment of a composition comprising PDE5 inhibitor(s), a pharmaceutical composition is provided, comprising: (a) tadalafil in an amount of 76.8% of the composition; (b) stearic acid in an amount of 6% of the composition; (c) glyceryl behenate in an amount of 20% of the composition; and (d) ascorbic acid in an amount of 0.2% of the composition.

In an eleventh embodiment of a composition comprising PDE5 inhibitor(s), a pharmaceutical composition is provided, comprising: (a) tadalafil in an amount ranging from 76.8-86.8% of the composition; (b) stearic acid in an amount of 6% of the composition; (c) glyceryl palmitostearate, in an amount ranging from 10-20% of the composition; and (d) ascorbic acid in an amount of 0.2% of the composition.

In a twelfth embodiment of a composition comprising PDE5 inhibitor(s), a pharmaceutical composition is provided, comprising: (a) tadalafil in an amount of 86.8% of the composition; (b) stearic acid in an amount of 6% of the composition; (c) glyceryl palmitostearate in an amount of 10% of the composition; and (d) ascorbic acid in an amount of 0.2% of the composition.

In a thirteenth embodiment of a composition comprising PDE5 inhibitor(s), a pharmaceutical composition is provided, comprising: (a) tadalafil in an amount of 76.8% of the composition; (b) stearic acid in an amount of 6% of the composition; (c) glyceryl palmitostearate in an amount of 20% of the composition; and (d) ascorbic acid in an amount of 0.2% of the composition.

In a fourteenth embodiment of a composition comprising PDE5 inhibitor(s), a pharmaceutical composition is provided, comprising: (a) one or more PDE5 inhibitor(s) in an amount ranging from 70.0-95.0% of the composition; (b) one or more pharmaceutically acceptable lubricants in an amount ranging from 6.0-15.0% of the composition; and (c) ascorbic acid in an amount of 0.2% of the composition.

In some embodiments, the composition comprises: (a) one or more PDE5 inhibitor(s) in an amount ranging from 80.0-90.0% of the composition; (b) one or more pharmaceutically acceptable lubricants in an amount ranging from 10.0-13.0% of the composition; and (c) ascorbic acid in an amount of 0.2% of the composition.

In some embodiments, the composition comprises: (a) one or more PDE5 inhibitor(s) in an amount ranging from 82.6-87.0% of the composition; (b) one or more pharmaceutically acceptable lubricants in an amount ranging from 10.5-12.4% of the composition; and (c) ascorbic acid in an amount of 0.2% of the composition.

In some embodiments, a pharmaceutical composition is provided, which comprises: (a) tadalafil in an amount of 86.8% of the composition; (b) stearic acid in an amount of 6% of the composition; and (c) ascorbic acid in an amount of 0.2% of the composition.

In some embodiments, the composition comprises: (a) tadalafil in an amount of 76.8% of the composition; (b) stearic acid in an amount of 6% of the composition; and (c) ascorbic acid in an amount of 0.2% of the composition.

In some embodiments, the composition further comprises one or more pharmaceutically acceptable vehicles in an amount ranging from 2.0-6.0% of the composition; and/or one or more antioxidants in an amount of ≤1% of the composition.

The amount of tadalafil in the composition can vary. In some embodiments, the amount of tadalafil in the composition ranges from 1 mg-2,000 mg, in some embodiments from 25 mg-2,000 mg, in some embodiments from 25 mg-100 mg, in some embodiments from 100 mg-200 mg, in some embodiments from 200 mg-1,200 mg, in some embodiments from 200 mg-800 mg, and in some embodiments from 200 mg-600 mg. In some embodiments, the amount of tadalafil in the composition is selected from 200 mg, 600 mg, 800 mg, 1200 mg and 2000 mg. In some embodiments, the amount of tadalafil in the composition is 25 mg. In some embodiments, the amount of tadalafil in the composition is 100 mg. In some embodiments, the amount of tadalafil in the composition is 200 mg. In some embodiments, the amount of tadalafil in the composition is 600 mg. In some embodiments, the amount of tadalafil in the composition is 800 mg. In some embodiments, the amount of tadalafil in the composition is 1,200 mg. In some embodiments, the amount of tadalafil in the composition is 2,000 mg.

In some embodiments, the amount of tadalafil in the composition is 25 mg and the composition is formulated to slowly erode upon administration to a subject over a period of 80-100 days, in some embodiments over a period of 90 days.

In some embodiments, the amount of tadalafil in the composition is 100 mg and the composition is formulated to slowly erode upon administration to a subject over a period of 80-100 days, in some embodiments over a period of 90 days.

In some embodiments, the amount of tadalafil in the composition is 200 mg and the composition is formulated to slowly erode upon administration to a subject over a period of 80-100 days, in some embodiments over a period of 90 days.

In some embodiments, the amount of tadalafil in the composition is 600 mg and the composition is formulated to slowly erode upon administration to a subject over a period of 5-7 months, in some embodiments over a period of 6 months.

In some embodiments, the amount of tadalafil in the composition is 800 mg and the composition is formulated to slowly erode upon administration to a subject over a period of 5-7 months, in some embodiments over a period of 6 months.

In some embodiments, the amount of tadalafil in the composition is 1200 mg and the composition is formulated to slowly erode upon administration to a subject over a period of up to 9 months.

In some embodiments, the amount of tadalafil in the composition is 2,000 mg and the composition is formulated to slowly erode upon administration to a subject over a period of up to 9 months.

Production of Pharmaceutical Compositions

In various aspects, the disclosed pharmaceutical compositions are compounded formulations that are generated according to methods suitable for use in a traditional compounding pharmacy. In some embodiments production methods suitable for use in non-traditional compounding pharmacies may be employed.

In a general sense, pharmaceutical compounding relates to the generation of a pharmaceutical product that is suited to the needs of an individual subject (such as those products produced pursuant to Section 503A of the U.S. Drug Quality and Security Act (DQSA) of 2013) or group of subjects (such as those products produced pursuant to Section 503B of the U.S. DQSA). To accomplish this, a compounding pharmacist combines active pharmaceutical ingredients with one or more pharmaceutically acceptable vehicles, and optionally one or more additional ingredients, into a formulation using various tools that can include, for example, specialized equipment.

In various aspects, the pharmaceutical compositions provided by the present disclosure are compounded via the use of a pellet press. There are several suitable pellet presses available that will be suitable to produce the disclosed compositions. An example of a pellet press suitable for use in the generation of the disclosed compositions is a Parr 2811 Pellet Press, which is capable of making a single pellet at a time. Other pellet presses exist that are capable of producing a plurality (e.g., a dozen, 100, several hundred, etc.) of pellets at once. A pellet press can be manual or automated.

An example of one suitable method of producing the disclosed pharmaceutical compositions follows. In this example, the pharmaceutical compositions are prepared using a pellet press capable of producing a single, pressed pellet at a time.

The first portion of the process can be performed using sterile technique outside of a clean room environment.

First, the individual components of the desired pharmaceutical composition are obtained and weighed. Preparation for the production of more than one pellet composition at a time can help reduce weighing errors. For example, if a 200 mg pellet of naltrexone is desired, preparing a lot of 100 to 400 of the 200 mg pellets at once affords the benefit of weighing out greater quantities of each of the composition components, which ensures greater accuracy. This may reduce, if not eliminate, errors associated with weighing small amounts of the components and will help produce a uniform pellet.

The weight of the ingredients can be optionally verified by weighing again on a separate scale. This helps to ensure that the compositions are created accurately, which will improve dosing.

Next, the components of the pharmaceutical compositions are triturated via geometric dilution.

Trituration is a method of processing materials, such as the components of a pharmaceutical composition, by grinding the components together. Trituration therefore typically involves reducing a substance to a smaller size.

Geometric dilution is a process by which a small amount (such as 200 mg) of an opioid antagonist or (25 or 100 mg) PDE5 inhibitor is mixed with one or more substances which help bind the antagonist so that it may be pressed into pellets form and/or provide other desirable properties to the resulting composition. Geometric dilution ensures equal distribution of the opioid antagonist(s) or PDE5 inhibitor(s) throughout the resulting composition.

In some embodiments, each of the individual components of the disclosed pharmaceutical compositions is a powder and/or each is capable of being powdered through physical manipulation, such as grinding. When the components of the pharmaceutical compositions are triturated via geometric dilution, a glass mortar and pestle may be employed to grind together equal parts of the composition components in small-batch quantities, adding the same amount of each substance and repeating the process until the entire amount of each of the individual components has been mixed together. The result of trituration via geometric dilution is that the individual components of the desired composition will be uniformly distributed in a single mixture. The mixture will be homogeneous, completely uniform in composition with respect to each component.

Thereafter, individual aliquots of the mixture are weighed out for pressing within a powder containment hood for employee protection, under non-sterile conditions, in a negative pressure room. To ensure accuracy in dosing, each aliquot is measured out and recorded so that they are all within an acceptable range of total weight.

For example, each aliquot may be measured such that it is within a range of 3%-5% of the desired weight of the pellet. In some embodiments, this calculation proceeds as follows:

Add together the total weight of all of the components, to achieve a total (a).

Divide the amount of (a) by the total number of pellets to be produced in the batch (e.g., 10, 50, 100, 200, 250, 300, etc.) and multiply that number by 1,000 to arrive at value (b). This should be the total desired weight of each pellet.

Add 3% to weight (b) to get to amount (c).

Add 5% to weight (b) to get to amount (d).

The weight of each individual aliquot will fall within the range of (c) and (d).

Divide the mixture into individual aliquots, each falling within the range of (c) to (d). Each individual aliquot can be weighed into a weigh boat, for example, or other suitable container.

At this point, the aliquots are moved into a clean room under negative pressure for pressing. In some embodiments, pellets can be pressed using a manual pellet press process. In some embodiments, pellets can be pressed using an automated pellet press process.

The pellet press may be located in a bio-safety cabinet inside of a clean room meeting prevailing ISO standards, as defined by USP, or the relevant state board of pharmacy regulations, to reduce the likelihood that the pressed pellets become contaminated. Because these pellets will be administered subcutaneously, preparation inside of a clean room will reduce the chance of negative side effects (e.g., infection) that may occur via the presence of contaminants. Although each pellet will be sterilized at the end of the process, the use of aseptic technique to weigh out and triturate components, followed by the pressing of pellets by a press located in a clean room, minimizes, if not completely eliminates, the risk of contamination.

In various embodiments, the manual pellet press is clean and has been sanitized using procedures consistent with clean room protocol.

The manual pellet press comprises a pellet die that is used to form the pellet. The die comprises a cylindrically shaped receptacle, for receiving the aliquot, and a punch that fits snugly within the interior diameter of the cylindrical receptacle. The aliquot can be poured into the open end of the die, such that it is received within the interior diameter of the die. The punch can then be moved into the interior diameter of the die and, using pressure applied by the pellet press, the punch compresses the aliquot into a pellet that is them the shape of the interior chamber of the die.

For either manual or automated pellet presses, the interior diameter of the pellet die can vary, depending upon the size of the pellet desired and/or the amount of opioid antagonist(s) or PDE5 inhibitor(s) to be pressed into a pellet. In some embodiments, the opioid antagonist is naltrexone, the amount of naltrexone present in the aliquot is 200 mg, and the interior diameter of the pellet die is selected from 0.25 inches (6.35 mm) and 0.125 inches (3.175 mm). In some embodiments, the opioid antagonist is naltrexone, the amount of naltrexone present in the aliquot is 600 mg, and the interior diameter of the pellet die is 0.375 inches (8 mm). In some embodiments, the opioid antagonist is naltrexone, the amount of naltrexone present in the aliquot is 800 mg, and the interior diameter of the pellet die is 0.5 inches (12.7 mm). In some embodiments, the opioid antagonist is naltrexone, the amount of naltrexone present in the aliquot is 1,200 mg, and the interior diameter of the pellet die is 0.5 inches (12.7 mm).

In some embodiments, the PDE5 inhibitor is tadalafil, the amount of tadalafil present in the aliquot is 25 mg, and the interior diameter of the pellet die is selected from 0.25 inches (6.35 mm) and 0.125 inches (3.175 mm). In some embodiments, the PDE5 inhibitor is tadalafil, the amount of tadalafil present in the aliquot is 50 mg, and the interior diameter of the pellet die is selected from 0.25 inches (6.35 mm) and 0.125 inches (3.175 mm). In some embodiments, the PDE5 inhibitor is tadalafil, the amount of tadalafil present in the aliquot is 100 mg, and the interior diameter of the pellet die is selected from 0.25 inches (6.35 mm) and 0.125 inches (3.175 mm). In some embodiments, the PDE5 inhibitor is tadalafil, the amount of tadalafil present in the aliquot is 200 mg, and the interior diameter of the pellet die is selected from 0.25 inches (6.35 mm) and 0.125 inches (3.175 mm). In some embodiments, the PDE5 inhibitor is tadalafil, the amount of tadalafil present in the aliquot is 600 mg, and the interior diameter of the pellet die is 0.375 inches (8 mm). In some embodiments, the PDE5 inhibitor is tadalafil, the amount of tadalafil present in the aliquot is 800 mg, and the interior diameter of the pellet die is 0.5 inches (12.7 mm). In some embodiments, the PDE5 inhibitor is tadalafil, the amount of tadalafil present in the aliquot is 1,200 mg, and the interior diameter of the pellet die is 0.5 inches (12.7 mm).

The manual pellet press can be calibrated by pouring a single aliquot into the die and pressing the powder into a pellet. Calibration is performed in order to determine the proper operating tension for the pellet press. Too little tension will not press the pellets properly. Too much tension will not allow the handle of the press to completely depress, which will create unwanted "skirts" on the bottom of the pellets.

The movable base, or anvil, of the manual pellet press is then fixed in place, in order to create uniformity in pellet size. This may be done by any means, including wrapping with adhesive tape, plastic wrap, and the like. The type of material used can vary, provided that it is sufficient to create uniform pellet size and it is sanitized when put into use.

The remainder of the batch of pellets can then be made. Each of the remaining aliquots can be poured into the die.

In some embodiments, the aliquots are poured into the die and pressed incrementally. For example, a small amount of the aliquot is initially poured into the die and pressed. Thereafter, more of the aliquot is poured into the die, on top of the amount that was previously pressed, and pressed. This process is repeated until the entire aliquot is poured into the die and pressed, thereby creating a pellet.

In some embodiments, the entirety of the aliquot is poured into the die and pressed once, thereby creating a pellet.

After the pellets have been pressed using a manual pellet press, the lower die is turned over and the pellets are pressed out. Each pellet may be retrieved from the press in its own container, or the pellets may be aggregated together in a single container.

In some embodiments, pellets can be pressed using an automated pellet press process. In some embodiments using an automated pellet press, the powder containing the components of the pharmaceutical compositions described herein can be loaded into a filling container and then pressed into the desired pellet size.

In some embodiments, pellets can be pressed using a modified tablet press. In such embodiments, the powder containing the components of the pharmaceutical composition described herein is prepared as a batch, weighted, triturated, and added to a feeding bin. The powder is then transferred automatically into a die and pressed. In some embodiments, the modified tablet press is automated and the pressing occurs at a faster rate than a manual press.

To ensure uniformity in weight, each pellet can be weighed to ensure that the final weight of the pellets is within the (c) to (d) range described above. Alternatively, random samples of pellets may be taken for weighing, for example 1 out of every 25 pellets pressed.

After receipt of confirmation that the pressed batch of pellets is within the proper weight range, the pellets are transferred into their final packaging, and subsequently sterilized.

Prior to sterilization, each pellet can be moved into its own container. In some embodiments, as noted above, this occurs upon removal of the pellet from the press die. Sterilizing each pellet in its own, sealed container ensures that it will be sterile when administered to a subject.

The type of container that may be utilized for sterilization and transport can vary. In some embodiments, each pellet is moved to a borosilicate glass vial. The glass vial defines an interior volume that is large enough to receive the pellet, but not so large that the pellet will freely move, as that can increase the risk of damage to both the pellet and the vial during transport. In some embodiments, the glass vial has been depyrogenated prior to addition of a pellet. In some embodiments, the glass vial comprises a PTFE (polytetrafluoroethylene)-sealed phenolic top or lid. In some embodiments, the glass container contains a radiation indicator. In some embodiments, prior to irradiation, a radiation indicator is affixed to the phenolic top or lid. In some embodiments, prior to irradiation, the container or vial has a label affixed to it, and in some embodiments the label contains a radiation indicator. For example, in some embodiments the opioid antagonist is naltrexone, the amount of naltrexone in the pellet is 200 mg and the glass vial is suitable in size, for example a glass vial that defines an inner volume of 2.5 ml. In other embodiments, for example, the PDE5 inhibitor is tadalafil, the amount of tadalafil in the pellet is 100 mg and the glass vial is suitable in size, for example a glass vial that defines an inner volume of 2.5 ml. Each vial may be labeled with the contents, the lot number, and batch beyond-use-date, and a tamper-resistant seal is added.

Figure 1B:
Figure 1C:
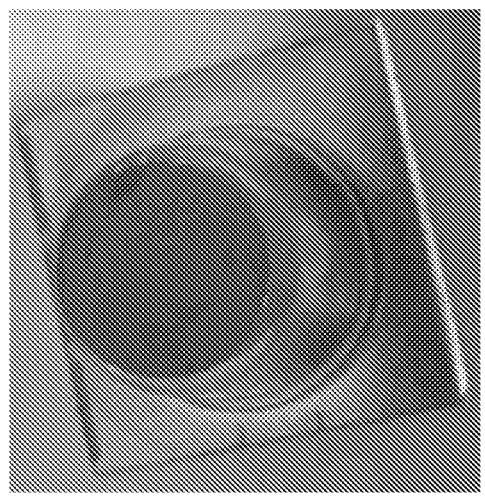

In some embodiments, the container is an amber, Polyvinylidene Chloride (PVdC), plastic blister pack and each pellet is moved into its own blister pack prior to sterilization. In some embodiments, the blister pack contains an external PVdC blister, a foil linter, and an indicator label. In some embodiments, the label contains a radiation indicator. An example of blister packs that are suitable for use with the disclosed process is shown in FIGS. 1A-1C, which provide three views of the same blister pack, with a pellet inside of it. This packaging and corresponding labels meet specifications outlined in USP 27 Section ≤671>, Class A, providing container closure integrity for up to 1 year.

In the depicted embodiment, a radiation indicator that changes color when the contents of the blister pack have been sterilized is affixed to the bottom of the blister pack. This indicator allows for visual validation and verification of the sterilization process. In some embodiments, this feature is incorporated into the label of the blister pack. The blister packaging system has the advantage of being a USP-approved means of storage and transport, it is time and cost-effective, and far less delicate than glass vials.

Once the pellets are inside of individual containers, they are ready for sterilization.

In some embodiments, the pellets are sterilized by autoclaving (moist-heat sterilization). In some embodiments, the pellets are sterilized by electron beam irradiation (e-beam sterilization). In some embodiments, the pellets are sterilized by gamma radiation sterilization. In some embodiments, the pellets are sterilized by x-ray. In some embodiments, the pellets are sterilized by dry heat sterilization.

Autoclaving the pellets entails moving the individual containers into an autoclave for sterilization via steam. The autoclave subjects the pellets, located inside of their respective containers, to high temperature and pressure.

Electron irradiation, also known as electron beam processing or e-beam processing, is a process whereby the pellets are subjected to high-energy beta radiation, in some embodiments under elevated temperatures and under a nitrogen atmosphere. The pellets, located within their respective containers, are passed under an electron beam that is produced by a high-energy electron beam accelerator.

E-beam processing introduces breaks in the nucleic acids of living organisms, such as microorganisms and viruses. The number of breaks is quite severe, such that e-beam irradiation results in microbial death, rendering the pellets and their respective containers sterile. E-beam processing has been accepted for use in the sterilization of medical products, such as the disclosed pharmaceutical compositions, and aseptic packaging materials utilized to transport the disclosed compositions.

Sterilization via e-beam processing provides advantages over sterilization via autoclaving, and other known methods of sterilization. It is a very fast process, it is compatible with a wide variety of materials, and does not require any quarantine following sterilization—the pellets are available for final testing and use in a subject, per the International Organization for Standardization standard number ISO 11137-2-2:2013.

Final testing on pellets may vary depending on the jurisdiction and can include, for example, successful results from a USP <85> endotoxin test, and in some situations, the additional successful completion of a USP <71> sterility test. At this point, the pharmaceutical compositions are available for administration to a subject.

Uses

The compositions disclosed herein can be used to treat subjects suffering from diseases, disorders, conditions, and symptoms for which opioid antagonists or PDE5 inhibitors are known to provide or are later found to provide therapeutic benefit.

As noted above, opioid antagonists are receptor antagonists that act on one or more of the opioid receptors. In some instances, opioid antagonists are competitive antagonists that bind to an opioid receptor with a higher affinity than the opioid (the agonist) itself. However, an antagonist does not activate the opioid receptor; rather, it blocks the receptor and prevents a biological response, such as responding to opioids and/or endorphins.

Some opioid antagonists, such as nalorphine and levallorphan, produce analgesic effects when administered in high doses to opioid-naive individuals.

Naloxone and nalorphine demonstrate weak partial agonist effects and are thus useful for long-term maintenance for certain subjects, such as former opioid addicts, and also for treating opioid overdose.

Naltrexone can be used to treat opioid addiction by blocking the effects of opioid drugs at the site of the receptor. A sustained course of low-dose naltrexone reverses the altered homeostasis which results from long-term abuse of opioid agonist drugs. Administration of naltrexone is also the only treatment currently available that can reverse the effects of post-acute withdrawal syndrome.

Naltrexone is also useful for the treatment of alcohol addiction or alcoholism. Naltrexone has been shown to be clinically efficacious in decreasing the amount and frequency of drinking.

Naltrexone is also useful for the treatment of amphetamine addiction. Naltrexone has been shown to be clinically efficacious in decreasing amphetamine usage.

Naltrexone and 6β-naltrexol, its active metabolite, are antagonists of the μ-opioid receptor, κ-opioid receptor, and δ-opioid receptor. Affinity values ($K_i$) of naltrexone at these receptors have been reported as 0.0825 nM (μ receptor), 0.509 nM (κ receptor), and 8.02 nM (δ receptor). 6β-naltrexol is reported to have lower affinity values ($K_i$), particularly the μ receptor affinity has been reported as half of that of naltrexone.

Naltrexone is a substituted oxymorphone, or more specifically the N-cyclopropylmethyl derivative of oxymorphone. As noted above, naltrexone is metabolized to its active metabolite, 6β-naltrexol. This metabolism is accomplished in a subject's system by the dihydrodiol dehydrogenase enzyme. Other metabolites exist and are detectable in a subject after administration of naltrexone, though their clinical significance, if any, is not yet known.

The plasma half-life of naltrexone and 6β-naltrexol are about 4 hours and 13 hours, respectively.

Naltrexone's antagonistic blockade of opioid receptors is the basis behind its mechanism of action and the principle on which it may be used to manage opioid dependence. It reversibly blocks, or attenuates, the effects of opioid drugs at the opioid receptor level. Its mechanism of action in alcohol dependence is still under investigation, but it is presently thought to be via modulation of the dopaminergic mesolimbic pathway.

As noted above, PDE5 inhibitors are drugs that block the degradative action of cGMP-specific phosphodiesterase 5 (PDE5) on cyclic GMP in smooth muscle cells, leading to an increased amount of cGMP and thus smooth muscle relaxation and increased blood flow. Such smooth muscle cells line the blood vessels supplying the corpus cavernosum of the penis. Thus, when present during sexual stimulation, PDE5 inhibitors can cause an increase in blood flow and erection. Sexual stimulation is required to initiate the local release of nitric oxide (the stimulator of cGMP), and therefore PDE5 inhibitors, such as, for example, tadalafil, have no sexual effect in the absence of sexual stimulation.

In a similar manner, PDE5 inhibitors can also influence the smooth muscle cells which line the blood vessels of the arterial wall of the lungs, for the relief of pulmonary hypertension. PDE5 inhibitors can also influence the concentration of cGMP in the smooth muscle of the prostate, the bladder, and their vascular supply, for the relief of the symptoms of benign prostatic hyperplasia.

PDE5 inhibitors preferentially inhibit PDE5, but at high doses, are not selective and certain PDE5 inhibitors are also known to inhibit other phosphodiesterase enzymes including PDE5, PDE6, PDE9, and PDE11. Specifically, tadalafil has been seen to inhibit PDE5 and PDE11 and sildenafil has been seen to inhibit PDE6 and PDE9.

In some embodiments, the PDE5 inhibitor is tadalafil. Tadalafil is a selective inhibitor of cyclic guanoside monophosphate PDE5. The known commercial version of tadalafil, marketed by Lilly ICOS, LLC, has a molecular weight of 389.41, the empirical formula of $C_{22}H_{19}N_3O_4$ and a chemical designation of pyrazino[1',2':1,6]pyrido[3,4-b]indole-1,4-dione, 6-(1,3-benzodioxol-5-yl)-2,3,6,7,12,12a-hexahydro-2-methyl-, (6R,12aR)-.

The plasma half-life of tadalafil is 17.5 hours. The plasma half-life of sildenafil and vardenafil are both 5-7 hours. Tadalafil is metabolized in the liver through the commonly used hepatic CYP3A4 enzyme system, which can simultaneously be engaged by other drugs or agents, thus shortening the half-life of tadalafil.

A sustained course of low-dose PDE5 inhibitors may allow for the restoration of normal erectile function, generalized inflammation reduction, and/or an improvement in a subject's testosterone to estrogen ratio.

Tadalafil can also be useful for the treatment of pulmonary hypertension. Tadalafil has beneficial effects in this treatment as it is believed to lower pulmonary arterial pressure and pulmonary vascular resistance by increasing pulmonary artery vasodilation and inhibiting vascular remodeling.

Tadalafil is also useful for the treatment of benign prostatic hyperplasia. Tadalafil has beneficial effects in this treatment as it is believed increase vasodilation in the smooth muscle of the prostate and bladder and accordingly to reduce symptoms.

Methods of treating a disease in a subject provided by the present disclosure comprise administering to a subject in need of such treatment a therapeutically effective amount of one or more opioid antagonists or PDE5 inhibitors. In various aspects, administration is accomplished by subcutaneous implantation of a composition provided by the present disclosure. The disclosed compositions provide therapeutic and/or prophylactic plasma and/or blood concentrations of one or more opioid antagonists or PDE5 inhibitors following subcutaneous implantation into a subject. The amount of opioid antagonist or PDE5 inhibitor administered can vary and can follow a dosing schedule that is appropriate for treatment of a particular disease.

In various aspects, the compositions provided by the present disclosure provide an extended release of one or more opioid antagonist(s) or PDE5 inhibitor(s) over a period of time. For example, a composition provided by the present disclosure can be formulated to provide a daily dose of the opioid antagonist naltrexone to a subject or to provide a daily dose of the PDE5 inhibitor tadalafil to a subject. In that regard, the composition is prepared and implanted into a subject subcutaneously. Thereafter, the composition erodes at a relatively constant daily rate, releasing a constant daily dose of naltrexone or tadalafil to the subject for the duration of time in which the composition exists within the subject's body. The naltrexone or tadalafil moves away from the implanted composition and into the subject's tissues, where it is then absorbed into the subject's blood stream.

In some embodiments, the opioid antagonist is naltrexone and the naltrexone is provided to a subject in a composition provided by the present disclosure by subcutaneously implanting the composition in the subject. In such embodiments, the metabolite 6β-naltrexol will be present in the subject as well, as a metabolite of naltrexone. An appropriate dose of naltrexone may be determined based on several factors, including, for example, the body weight and/or condition of the subject being treated, the severity of the disease being treated, the incidence and/or severity of side effects, the manner of administration, the metabolism of the subject, the genetic makeup of the subject, and the judgment of the prescribing physician.

Blood levels of naltrexone may range from about 1 ng/ml to about 50 ng/ml, from about 2 ng/ml to about 36 ng/ml, about 2 ng/ml to about 26 ng/ml, and in certain embodiments, from about 3 ng/ml to about 10 ng/ml. Blood levels of 6β-naltrexol may range from about 1 ng/ml to about 50 ng/ml, from about 34 ng/ml to about 52 ng/ml.

In some embodiments, compositions provided by the present disclosure comprise naltrexone and are administered to a subject to treat a disorder selected from alcoholism, amphetamine addiction, opioid addiction, and combinations thereof.

In some embodiments, the PDE5 inhibitor is tadalafil and the tadalafil is provided to a subject in a composition provided by the present disclosure by subcutaneously implanting the composition in the subject. An appropriate dose of tadalafil may be determined based on several factors, including, for example, the body weight and/or condition of the subject being treated, the severity of the disease being treated, the incidence and/or severity of side effects, the manner of administration, and the judgment of the prescribing physician.

In some embodiments, compositions provided by the present disclosure comprise tadalafil and are administered to a subject to treat a disorder selected from erectile dysfunction, pulmonary hypertension, benign prostatic hyperplasia, and combinations thereof.

In certain embodiments, a therapeutically effective dose of an opioid antagonist or PDE5 inhibitor may provide therapeutic benefit without causing substantial toxicity including adverse side effects. Toxicity of naltrexone and/or metabolites thereof may be determined using standard pharmaceutical procedures and may be ascertained by those skilled in the art. A dose of naltrexone may be within a range capable of establishing and maintaining a therapeutically effective circulating plasma and/or blood concentration of naltrexone that exhibits little or no toxicity.

Administration

The pharmaceutical compositions disclosed herein may be administered by subcutaneous implantation or by any other appropriate route suitable for systemic administration of the opioid antagonist(s) or PDE5 inhibitor(s).

The amount of the opioid antagonist(s) or PDE5 inhibitor(s) that will be effective in the treatment of a disease in a subject will depend, in part, on the nature of the condition and can be determined by standard clinical techniques known in the art. In addition, in vitro or in vivo assays may be employed to help identify optimal dosage ranges. A therapeutically effective amount of an opioid antagonist or PDE5 inhibitor(s) to be administered may also depend on, among other factors, the subject being treated, the weight of the subject, the severity of the disease, the manner of administration, and the judgment of the prescribing physician.

For systemic administration, a therapeutically effective dose may be estimated initially from in vitro assays. For example, a dose may be formulated in animal models to achieve a beneficial circulating composition concentration range. Initial doses may also be estimated from in vivo data, e.g., animal models, using techniques that are known in the art. Such information may be used to more accurately determine useful doses in humans. One having ordinary skill in the art may optimize administration to humans based on animal data.

A dose may be administered in a single pharmaceutical composition or in multiple compositions. When multiple compositions are used the amount of the opioid antagonist(s) or PDE5 inhibitor(s) contained within each composition may be the same or different. The amount of the opioid antagonist(s) or PDE5 inhibitor(s) contained in a composition administered to a subject may depend on the route of administration and whether the disease in a subject is effectively treated by acute, chronic, or a combination of acute and chronic administration.

In certain embodiments, the expected amount of drug delivered on average from an administered dose is less than a toxic dose. Toxicity of the compositions described herein may be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. In certain embodiments, the opioid antagonist(s) or PDE5 inhibitor(s) may exhibit a high therapeutic index. The data obtained from these cell culture assays and animal studies may be used in formulating a dosage range that is not toxic to humans. A dose of the opioid antagonist(s) or PDE5 inhibitor(s) provided by the present disclosure may be within a range of circulating concentrations in for example the blood, plasma, or central nervous system, that include the effective dose and that exhibits little or no toxicity. A dose may vary within this range depending upon the dosage form employed and the route of administration utilized. In certain embodiments, an escalating dose may be administered.

In various aspects, pharmaceutical compositions provided by the present disclosure are administered via subcutaneous implantation. In some embodiments, following administration of either local or general anesthesia, the initial entry point may be made in the skin of a subject by use of a scalpel. In some embodiments, the compositions can be subcutaneously implanted in a subject via the use of a trocar device.

In some embodiments, the pharmaceutical compositions provided by the present disclosure are cylindrical in shape, having been generated by a pellet press. In such embodiments, the compositions can be subcutaneously implanted in a subject via the use of a trocar device.

Sterile technique is used to insert the compositions subcutaneously. This may include, without limitation, sterilization of each component of the trocar device prior to use, cleaning and sterilization of the insertion site, and proper sterilization of the pharmaceutical composition prior to implantation.

Kits

In a further aspect, kits are provided by the present disclosure, such kits comprising: one or more pharmaceutical compositions, each composition sterilized within a container, means for administration of the pharmaceutical compositions to a subject, and instructions for use.

In some embodiments, the kits comprise: (a) one or more naltrexone pellets, each pellet located within in its own plastic blister pack or borosilicate glass vial and each pellet having been e-beam processed or sterilized; (b) a trocar tray that includes all of the medical implements necessary to subcutaneously implant the pellets into a subject; and (c) instructions for using the trocar tray to subcutaneously implant the pellets in a subject.

In some embodiments, the kits comprise: (a) one or more tadalafil pellets, each pellet located within in its own plastic blister pack or borosilicate glass vial and each pellet having been e-beam processed or sterilized; (b) a trocar tray that includes all of the medical implements necessary to subcutaneously implant the pellets into a subject; and (c) instructions for using the trocar tray to subcutaneously implant the pellets in a subject.

EXAMPLES

The following examples illustrate various aspects of the disclosure. It will be apparent to those skilled in the art that many modifications, both to materials and methods, may be practiced without departing from the scope of the disclosure.

Generation of Opioid Antagonist Pellets

Several batches of naltrexone pellets were prepared as follows:

Each ingredient, naltrexone and the added pharmaceutically acceptable vehicle(s), was separately weighed and the weight verified.

The ingredients were mixed together via trituration and geometric dilution, as described herein, to ensure uniformity in the mixture.

The uniform mixture was divided into one or more samples containing naltrexone in portions for pelleting (e.g., 200 mg, 600 mg, 800 mg, or 1,200 mg portions).

To generate an individual pellet, a single portion was incrementally poured into the die of a Par 2811 Pellet Press and pressed into a pellet. For example, when generating 200 mg pellets, a small amount of the 200 mg portion was initially poured into the die and pressed. Thereafter, more of the 200 mg portion was poured into the die, on top of the previously pressed amount, and pressed. This process was repeated until the entire 200 mg portion was poured into the die and pressed, thereby creating a 200 mg pellet.

The die was turned over and the pellet removed to a weighing dish.

The final weight of each pellet was confirmed, for example, 200 mg, 600 mg, 800 mg, or 1,200 mg. In some instances, there may be loss of 3-5% of ingredients, resulting from the pelleting process. By way of example, an individual pellet was considered to contain 200 mg of naltrexone if it fell within a range of 180 mg to 220 mg as confirmed via quantitative analysis conducted by an independent laboratory.

The pellets were then sterilized, either by autoclaving or e-beam sterilization.

Pellets were initially formulated so they could be sterilized by either autoclave or eBeam. As described below, the initial batch of pellets produced (batch 1 in the first batches) was autoclaved, however autoclaving did not produce viable pellets. Adjusting autoclave temperatures and cycles in an attempt to improve sterilization efficacy made no difference. Additional formulations, sterilized by other means, were subsequently produced and successfully tested, confirming that the errors to batch 1 occurred because of attempted sterilization via autoclaving, rather than the formulation.

Example 1: Generation of 200 mg Opioid Antagonist Pellets

First Round Batches, 200 mg Naltrexone Pellets

In a first attempt at making opioid antagonist-containing pellets suitable for subcutaneous implantation in a subject, seven pellet batches of 200 mg pellets were prepared.

Povidone was utilized as a means of dispersing and suspending the naltrexone in the powder formulation, prior to pelleting, and to serve as a binder in the formed pellets. Stearic acid was utilized in order to lubricate and reduce the brittleness of the pellets. As these pellets need to withstand shipping to and from sterilization facilities and then subsequently for implantation into a subject, they must be resilient to friability. Pellets that are less brittle are less likely to break unintentionally.

The components of each batch from the First Round and their amounts are shown in Table 1.

TABLE 1

| | | Pellet Components | | |
|---|---|---|---|---|
| Batch | Naltrexone | Stearic Acid | Povidone K-30* | Pellets Made |
| 0 | 5.988 g | 0.078 g | 0.162 g | 30, 200 mg each |
| 1 | 59.88 g | 1.917 g | 1.620 g | 300, 200 mg each |
| 2 | 49.9 g | 1.598 g | 1.35 g | 250, 200 mg each |
| 3 | 49.9 g | 1.597 g | 1.35 g | 250, 200 mg each |
| 4 | 39.92 g | 1.278 g | 1.08 g | 200, 200 mg each |
| 5 | 1.996 g | 0.12 g | 0.054 g | 5, 200 mg each |
| 6 | 39.92 g | 1.278 g | 1.08 g | 200, 200 mg each |

*the povidone K-30 has an average molecular weight of 40,000 (CAS 9003-39-8)

Batch 0 was made to perfect the formulation and to validate the compounding method. That appeared to work well, dose validation results were received but none were returned for inspection. The remaining six batches were subsequently produced, however, none produced viable pellets. Batch 1 was autoclaved for sterilization and the pellets melted. The remaining batches were e-beam sterilized. However, these batches produced brittle pellets that did not survive transfer to and/or from sterilization. For example, 162 of the 250 pellets produced in batch 2 were broken during e-beam sterilization and/or transfer.

Endotoxin levels for all batches were exceedingly low, indicating the production of several batches of safe, pharmaceutically acceptable pellets. However, many of the pellets produced were either too brittle for implantation, too fragile for shipping and/or were negatively impacted by the sterilization process, for example by becoming severely discolored. The discoloration indicates oxidation of one or more of the formulation components, which may result in reduced and/or unpredictable dosing to a subject.

Second Round Batches, 200 mg and 1,000 mg Opioid Antagonist Pellets

The formulation was adjusted. In a second attempt at making opioid antagonist-containing pellets suitable for subcutaneous implantation in a subject, nine pellet batches were prepared, eight of 200 mg pellets and one of 1000 mg pellets. The components of each batch and their amounts are shown in Table 2.

TABLE 2

| | | Pellet Components | | | |
|---|---|---|---|---|---|
| Batch | Naltrexone | Stearic Acid | Povidone K-30* | Ascorbic Acid | Pellets Made |
| E | 1.996 g | 0.12 g | 0.054 g | 0.002 g | 10, 200 mg each |
| 0 | 49.91 g | 6.0 g | 1.35 g | 0.101 g | 250, 200 mg each |
| 1 | 49.9 g | 6.0 g | 1.35 g | 0.100 g | 250, 200 mg each |
| 2 | 5.988 g | 0.72 g | 0.162 g | 0.012 g | 30, 200 mg each |
| 3 | 55.889 g | 6.72 g | 1.512 g | 0.112 g | 280, 200 mg each |
| 4 | 59.88 g | 7.2 g | 1.62 g | 0.12 g | 300, 200 mg each |
| 5 | 59.88 g | 7.2 g | 1.62 g | 0.12 g | 300, 200 mg each |
| 6 | 39.92 g | 4.8 g | 1.08 g | 0.008 g | 200, 200 mg each |
| 7 | 2.994 g | 0.361 g | 0.0810 g | 0.006 g | 3, 1,000 mg each |

*the povidone K-30 has an average molecular weight of 40,000 (CAS 9003-39-8)

Batch E was the preferred formulation of three experimental batches produced to determine if the addition of varying amounts of ascorbic acid to the formulation would generate viable pellets. The result was positive; the addition of ascorbic acid generated 10 viable pellets. As that worked well, the remaining seven batches were produced.

In this instance, each batch produced viable pellets. Pellet loss due to friability/fragility was minimal in each batch. As with the first batches, endotoxin levels for all batches were exceedingly low, indicating the production of several batches of safe, pharmaceutically acceptable pellets.

It appeared that the combination of povidone and stearic acid helped to reduce the brittleness, and thus increase viability, of the pellets. The increased yield of viable pellets from the new formulation was surprising. The stearic acid was increased to help decrease rigidity/brittleness, though it was not expected that the combination of stearic acid with povidone would help to reduce the fragility of a compounded pellet. In an early test (data not shown), pellets were made with only 94% naltrexone and 6% stearic acid, no povidone or any other vehicle. Due to the hygroscopic nature of povidone, it was omitted to rule out any absorption of water in the sterilization process as the reason for failure. The resulting pellets were far more fragile than the pellets produced with the combination of povidone and stearic acid. Pellets pressed with 6% stearic acid and povidone were less rigid/fragile and thus were less apt to break.

Pellets pressed with 6% stearic acid, povidone and 0.1% ascorbic acid were still somewhat fragile, but the oxidation from the e-beam sterilization was markedly reduced. The total number of pellets lost to breakage was far less than the pellets produced in the first batches, however a further reduction in the total number lost was still desired. Increasing the ascorbic acid to 0.2%, with 6% stearic acid and povidone, reduced the oxidation even further, however the fragility of the pellets could still be improved.

Increasing the stearic acid from 0.12 grams per 10 pellets to 0.24 grams per 10 pellets dramatically reduced the brittleness of the pellets. Pellets produced with 12% stearic acid (0.24 g/10 pellets), 0.2% ascorbic acid (0.004 g/10 pellets) and 2.7% povidone were almost universally viable. Loss from breakage was virtually eliminated.

The addition of a small amount of ascorbic acid, at amounts as low as 0.1%, resulted in surprising effects. First, its addition made the pellets less fragile, resistant to breakage, and thus far more viable. Compared to the pellets made from the first batches, which did not have any ascorbic acid, the pellets of the second batches were far less brittle and the total numbers lost due to breaking was greatly reduced. It therefore appears that the combination of povidone, stearic acid and ascorbic acid produces pellets that are durable, consistent, uniform in color, not indurate, and resistant to breakage. Second, the ascorbic acid greatly reduced the oxidation that occurs during e-beam sterilization.

Adding ascorbic acid reduced the amount of naltrexone that oxidized, thus improving not only the aesthetic appearance, and also surprisingly increased the usable percentage of naltrexone present in the formulations, as verified by potency tests. Prior to the addition of ascorbic acid to any formulation, only a single batch produced achieved a potency of 91%, which is only minimally acceptable.

Following the addition of ascorbic acid, the pellets have had a more consistent color; batches displayed reduced breakage; and potency tests consistently returned values of 100%+. As noted in detail above, in addition to being a potent antioxidant, in the disclosed formulations ascorbic acid surprisingly appears to be assuming the role of a vehicle (a binder and/or filler), increases the usable percentage of naltrexone in the formulations and possesses chelating activity. Moreover, the amount of ascorbic acid added to the second batch formulations was substantially greater than the upper limit suggested by the monograph "*The Art, Science and Technology of Pharmaceutical Compounding*", Allen, L. 5e, which resulted in a superior product. This monograph provides limited information about the use of ascorbic acid in compounded pharmaceutical formulations and suggests the use of 0.01-0.1% ascorbic acid in aqueous formulations. It has no recommended range for solid dosage forms. Additionally, the monograph only refers to ascorbic acid as an antioxidant; it contains no suggestion that it can be used as a vehicle (binder or filler) or that it might display vehicle-like properties.

The amount of ascorbic acid added to the formulations disclosed herein is greater than the upper limit suggested by this monograph. This amount, which should be considered too high based on the disclosure provided by the monograph, resulted in a superior product.

Additionally, the addition of ascorbic acid is unlikely to result in negative side effects. Ascorbic acid, also known as vitamin C, is generally well tolerated by subjects and the total amount used in the exemplified formulations is small— roughly 40 micrograms per 200 mg pellet.

Surface area degradation calculations from the pellets produced in these second batches were performed. Based on the calculations, these pellets are expected to deliver a total dose of 800 mg, derived from the administration of four 200 mg pellets, of naltrexone to a subject constantly over an estimated period of 3 months, or roughly 1.3 to 2.1 mg of naltrexone per pellet per day.

Third Round Batches, 200 mg, 600 mg, and 1,200 mg Opioid Antagonist Pellets

The formulation was further adjusted, substituting glyceryl monostearate (GMS) for povidone. In a third iteration of making opioid antagonist-containing pellets suitable for subcutaneous implantation in a subject, seven pellet batches were prepared. The components of each batch and their amounts are shown in Table 3. Details regarding the production of each batch are provided in Examples 5 (200 mg pellets), 6 (600 mg pellets) and 7 (1,200 mg pellets).

TABLE 3

Pellet Components

| Batch | Naltrexone | Stearic Acid | GMS | Ascorbic Acid | Pellets Made |
|---|---|---|---|---|---|
| 1 (Control) | 0.996 g | — | 0.100 g | — | 5, 200 mg each |
| 2 (Control) | 0.997 g | — | 0.200 g | — | 5, 200 mg each |
| 3 | 0.996 g | 0.0301 g | 0.100 g | 0.0021 g | 5, 200 mg each |
| 4 | 0.997 g | 0.0300 g | 0.203 g | 0.0020 g | 5, 200 mg each |
| 5 | 2.689 g | 0.0811 g | 0.271 g | 0.0055 g | 4, 600 mg each |
| 6 | 2.689 g | 0.0810 g | 0.451 g | 0.0054 g | 4, 600 mg each |
| 7 | 35.854 g | 1.081 g | 3.602 g | 0.0724 g | 30, 1,200 mg each |

In this instance, batches 1-2 were control batches, the formulations containing only naltrexone and GMS (no ascorbic acid or stearic acid). These control formulations, containing just naltrexone and either 10% GMS (batch 1) or 20% GMS (batch 2), resulted in pellets that crumbled very easily with slight pressure.

Batches 3-7 produced viable pellets. Pellet loss due to friability/fragility was minimal. These batches were subjected to e-beam sterilization for visual and tactile validation.

As discussed in further detail below, in these third round batches, batch 3 was the best performing formulation, with the best consistency and appearance of pellets. Batch 5 also performed well, which had a smooth, slightly waxy feel to the 600 mg pellets.

The addition of a small amount of ascorbic acid, at amounts as low as 0.2%, resulted in surprising effects. As detailed above, its addition made the pellets less fragile, resistant to breakage, and thus far more viable. Compared to the pellets made from the first round of batches, which did not have any ascorbic acid, the pellets of the second and third round batches were far less brittle and the total numbers lost due to breaking was greatly reduced. It therefore appears that the combination of stearic acid and ascorbic acid produces pellets that are durable, consistent, uniform in color, not indurate, and resistant to breakage. The addition of stearic acid reduced the brittleness, and thus increased the viability of the pellets. This addition was not expected to further reduce the fragility of a compounded pellet.

As discussed above, following the addition of ascorbic acid, the pellets have had a more consistent color; even long after sterilization, the pellets maintained their slightly yellowish/off-white appearance. Higher percentages of GMS rendered a "crumblier" product. Adding ascorbic acid solved that problem.

Example 2: Generation of 600 mg Opioid Antagonist Pellets

In a third attempt at making opioid antagonist-containing pellets suitable for subcutaneous implantation in a subject using povidone as a vehicle, a single batch of 600 mg naltrexone pellets was prepared according to the method provided above ("Generation of Opioid Antagonist Pellets").

Because of the success in producing fully viable pellets in the second batch productions of 200 mg naltrexone pellets, the formulation was maintained in the generation of 600 mg pellets. To produce the pellets, the following components were used: 65.868 g naltrexone, 7.92 g stearic acid, 1.782 g povidone K-30 (average molecular weight of 40,000 (CAS 9003-39-8), and 0.132 g ascorbic acid.

An 8 mm die was used in the pellet press, in order to keep the diameter of the pellets as small as possible.

The batch produced viable pellets. Only 12 pellets were lost, but in the calibration process, not to breakage. The pellets were suitable for implantation into a subject.

Surface area degradation calculations from the pellets produced in these second batches were performed. Based on the calculations, these pellets are expected to deliver an estimated dose of 1,200 to 1,800 mg of naltrexone to a subject over a period of 6 months.

Example 3: Generation of 1,200 mg Opioid Antagonist Pellets

In a fourth attempt at making opioid antagonist-containing pellets using povidone, suitable for subcutaneous implantation in a subject, two batches of 1,200 mg naltrexone pellets were prepared according to the method provided above ("Generation of Opioid Antagonist Pellets").

As noted above, the formulation used to produce the 200 mg and 600 mg pellets successfully produced viable pellets. However, because of the increase in size of the 1,200 mg pellets, minor modifications to the formulation were required.

The components of both batches and their amounts are shown in Table 4.

TABLE 4

| | | Pellet Components | | | |
|---|---|---|---|---|---|
| Batch | Naltrexone | Stearic Acid | Povidone K-30* | Ascorbic Acid | Pellets Made |
| 1 | 35.928 g | 5.4 g | 2.052 g | 0.12 g | 30, 1200 mg each |
| 2 | 1.557 g | 0.234 g | 0.0889 g | 0.0052 g | 1, 1200 mg |

*the povidone K-30 has an average molecular weight of 40,000 (CAS 9003-39-8)

The pellets produced were viable, the total number of lost pellets was only 2 and only in the calibration process. The pellets from batch 0 were sent for batch validation testing and none were returned broken.

For a 1,200 mg formulation, a die with an increased diameter was required, in this example a die with a 0.5-inch diameter was utilized. Because of that, a larger pellet having greater surface area will be produced. Such pellets will be more susceptible to breaking/chipping. Therefore, the amount of stearic acid used in the formulation was increased from 12%, which was used in the 200 mg and 600 mg formulations, to 15%. Additionally, the amount of povidone was increased from 2.7%, which was used in the 200 mg and 600 mg formulations, to 5.7%. The amount of ascorbic acid was left at 0.2%. The pellets produced were almost universally viable. Loss from breakage was virtually eliminated.

Example 4: Generation of 2,000 mg Opioid Antagonist Pellets

In a fifth attempt at making opioid antagonist-containing pellets, using povidone as a vehicle, suitable for subcutaneous implantation in a subject, a single batch of 3, 2,000 mg naltrexone pellets was attempted according to the method provided above ("Generation of Opioid Antagonist Pellets").

As with the formulation generated to produce the 1,200 mg pellets of Example 3, minor modifications to the 200 mg and 600 mg formulation were required.

To produce the pellets, the following components were used: 2.5948 g naltrexone, 0.312 g stearic acid, 0.0702 g povidone K-30 (average molecular weight of 40,000 (CAS 9003-39-8), and 0.0052 g ascorbic acid. Viable pellets were not produced, as the pellet mold was unable to accept the entire aliquot of powder. A larger pellet mold may be able to accommodate the total amount and produce viable pellets.

Example 5: Generation of 200 mg Opioid Antagonist Pellets

In a sixth attempt at making opioid antagonist-containing pellets suitable for subcutaneous implantation in a subject, naltrexone pellets were attempted according to the method provided above ("Generation of Opioid Antagonist Pellets"), wherein povidone was substituted for glyceryl monostearate (GMS).

In the first 200 mg batch (10% GMS) (see Table 3, Batch 1), to produce the pellets, the following components were used: 0.996 g naltrexone and 0.100 g glycerol monostearate (GMS). No antioxidant was included in the formulation. The resulting pellets were crumbly, not at all suitable for patient use.

In the second 200 mg batch (20% GMS) (see Table 3, Batch 2), to produce the pellets, the following components were used: 0.996 g naltrexone and 0.200 g glycerol monostearate (GMS). Again, no antioxidant was included in the formulation. The resulting pellets were crumbly and not suitable for patient use. Without ascorbic acid, the pellets lack structural stability.

In the third 200 mg batch (10% GMS) (see Table 3, Batch 3), to produce the pellets, the following components were used: 0.996 g naltrexone, 0.0301 g stearic acid, 0.100 g glycerol monostearate (GMS), and 0.0021 g ascorbic acid. This batch included ascorbic acid and a small amount of stearic acid. The stearic acid aided in the removal of the pellets from the press. The resulting pellets had superior consistency and appearance and appear to be viable/suitable for patient use. Structural stability returned to the pellets with the addition of ascorbic acid, which was surprising. It was unexpected that the presence of ascorbic acid would provide structural stability to these naltrexone pellet formulations.

In the fourth 200 mg batch (20% GMS) (see Table 3, Batch 4), to produce the pellets, the following components were used: 0.997 g naltrexone, 0.03 g stearic acid, 0.203 g glycerol monostearate (GMS), and 0.002 g ascorbic acid. The resulting pellets were brittle; they were not crumbly, like the batches without ascorbic acid, but at 20% GMS seem unlikely to dissolve optimally after implantation.

Example 6: Generation of 600 mg Opioid Antagonist Pellets

In a seventh attempt at making opioid antagonist-containing pellets suitable for subcutaneous implantation in a subject, naltrexone pellets were attempted according to the method provided above ("Generation of Opioid Antagonist Pellets"), wherein povidone was substituted for glyceryl monostearate (GMS).

In the first 600 mg batch (10% GMS) (see Table 3, Batch 5), to produce the pellets, the following components were used: 2.689 g naltrexone, 0.0811 g stearic acid, 0.271 g glycerol monostearate (GMS), and 0.0055 g ascorbic acid. The resulting pellets were smooth with a slightly waxy feel. These pellets are suitable for use in patients.

In the second 600 mg batch (20% GMS) (see Table 3, Batch 6), to produce the pellets, the following components were used: 2.689 g naltrexone, 0.0810 g stearic acid, 0.451 g glycerol monostearate (GMS), and 0.0054 g ascorbic acid. The resulting pellets were smooth, but too waxy. Again at 20% GMS, the pellets are unlikely to be suitable for patient use.

Example 7: Generation of 1,200 mg Opioid Antagonist Pellets

In an eighth attempt at making opioid antagonist-containing pellets suitable for subcutaneous implantation in a subject, naltrexone pellets were attempted according to the method provided above ("Generation of Opioid Antagonist Pellets"), wherein povidone was substituted for glyceryl monostearate (GMS). These pellets were utilized for e-beam dose validation.

In the 1,200 mg batch (10% GMS) (see Table 3, Batch 7), to produce the pellets, the following components were used: 35.854 g naltrexone, 1.081 g stearic acid, 3.602 g glycerol monostearate (GMS), and 0.0724 g ascorbic acid. The resulting pellets were viable, though large in size and unlikely to be desirable for use by patients as a consequence.

Example 8: Generation of PDE5-Inhibitor-Containing Pellets

Tadalafil pellets were prepared as follows:

Each ingredient, tadalafil and the added pharmaceutically acceptable vehicle(s), was separately weighed and the weight verified.

The ingredients were mixed together via trituration and geometric dilution, as described herein, to ensure uniformity in the mixture.

The uniform mixture was divided into one or more samples containing tadalafil in portions for pelleting (e.g., 200 mg, 600 mg, 800 mg, or 1,200 mg portions).

To generate an individual pellet, a single portion was incrementally poured into the die of a Par 2811 Pellet Press and pressed into a pellet. For example, when generating 800 mg pellets, a small amount of the 800 mg portion was initially poured into the die and pressed. Thereafter, more of the 800 mg portion was poured into the die, on top of the previously pressed amount, and pressed. This process was repeated until the entire 800 mg portion was poured into the die and pressed, thereby creating a 800 mg pellet.

The die was turned over and the pellet removed to a weighing dish.

The final weight of each pellet was confirmed, for example, 200 mg, 600 mg, 800 mg, or 1,200 mg. By way of example, the weight of an individual pellet was considered to be at 800 mg if it fell within a range of 720 mg to 880 mg.

The pellets were then sterilized by e-beam sterilization.

Example 9: Generation of 800 mg PDE5 Inhibitor-Containing Pellets

In a first attempt at making PDE5 inhibitor-containing pellets suitable for subcutaneous implantation in a subject, a batch of 800 mg pellets was prepared according to the method of Example 8.

Glyceryl monostearate (GMS) was utilized as a means of dispersing and suspending the tadalafil in the powder formulation, prior to pelleting, and to serve as a binder in the formed pellets. Ascorbic acid was added, with the hope that the surprising effects it displayed in the naltrexone pellets would be repeated in the tadalafil pellets. Stearic acid was utilized in order to lubricate and reduce the brittleness of the pellets. As these pellets need to withstand shipping to and from sterilization facilities and then subsequently for implantation into a subject, they must be resilient to friability. Pellets that are less brittle are less likely to break unintentionally.

The components of this batch of 800 mg pellets and their amounts are shown in Table 5.

TABLE 5

| Pellet Components | | | | |
|---|---|---|---|---|
| Tadalafil | Stearic Acid | GMS | Ascorbic Acid | Pellets Made |
| 23.380 g | 0.695 g | 2.322 g | 0.0464 g | 27, 800 mg each |

The addition of ascorbic acid to both the naltrexone and tadalafil formulations resulted in pellets having a more consistent color and greater structural stability (for example, reduced breakage, no crumbling, and the like). It therefore appears that ascorbic acid is acting as a binder in these formulations, as well as an antioxidant, as it did in the naltrexone pellets, described above.

The same effects seen in the naltrexone pellets were demonstrated in the tadalafil pellets. Briefly, in addition to being a potent antioxidant, in the tadalafil formulations ascorbic acid surprisingly appears to be assuming the role of a vehicle (a binder and/or filler) and possesses anti-fungal activity. Moreover, the amount of ascorbic acid added to the second batch formulations was substantially greater than the upper limit suggested by the monograph "*The Art, Science and Technology of Pharmaceutical Compounding*", Allen, L. 5e.

Example 10: Generation of 100 mg PDE5 Inhibitor-Containing Pellets

A batch of 100 mg tadalafil pellets PDE5 inhibitor-containing pellets suitable for subcutaneous implantation in a subject using GMS as a vehicle is prepared according to the method provided in Example 8.

To produce the pellets, the following components are used: tadalafil, stearic acid, GMS, and ascorbic acid, in the amounts recited in Table 5.

Example 11: Implantation of 200 mg Naltrexone-Containing Pellets

Figure 2:
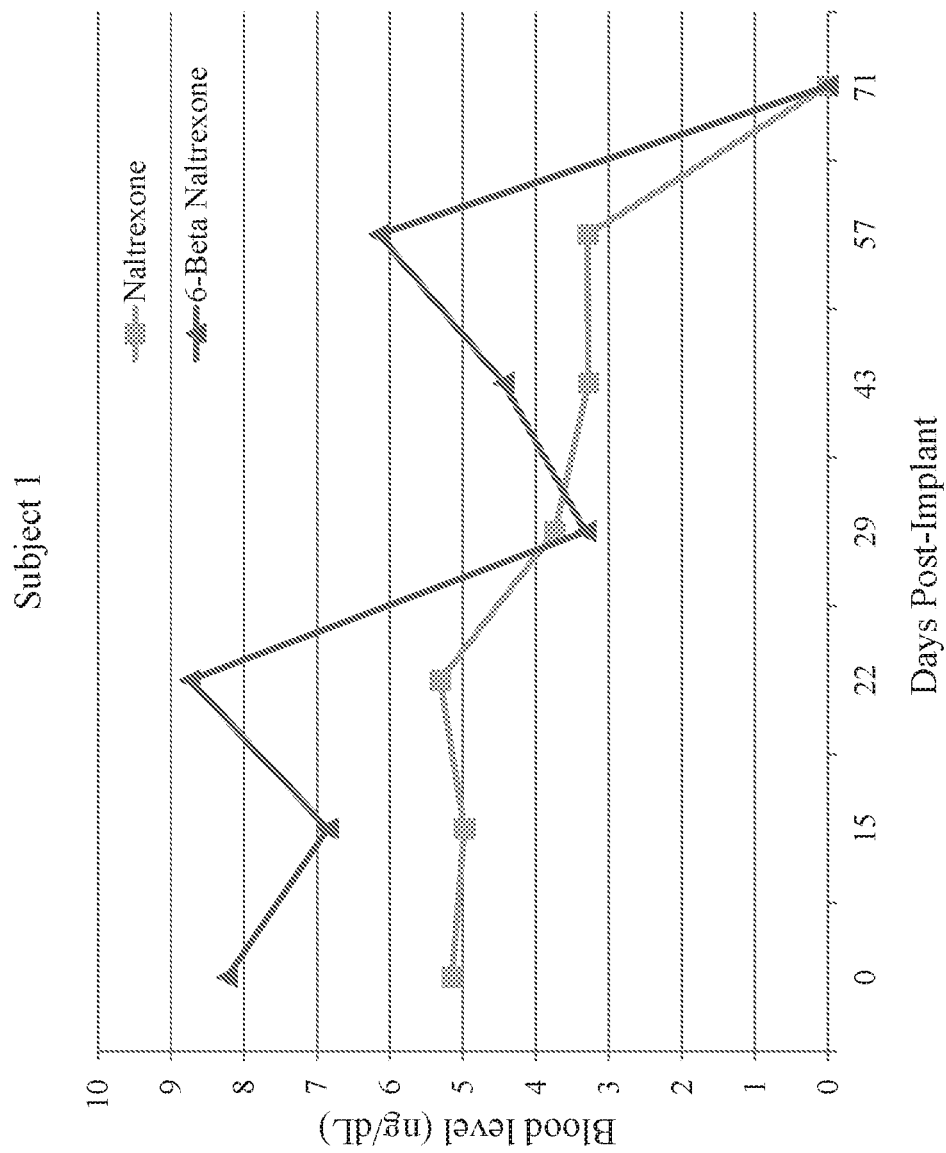
FIG. 2 shows naltrexone and 6-beta naltrexone blood levels over time in a first human subject implanted with a naltrexone-containing pellet, according to some embodiments.
Figure 3:
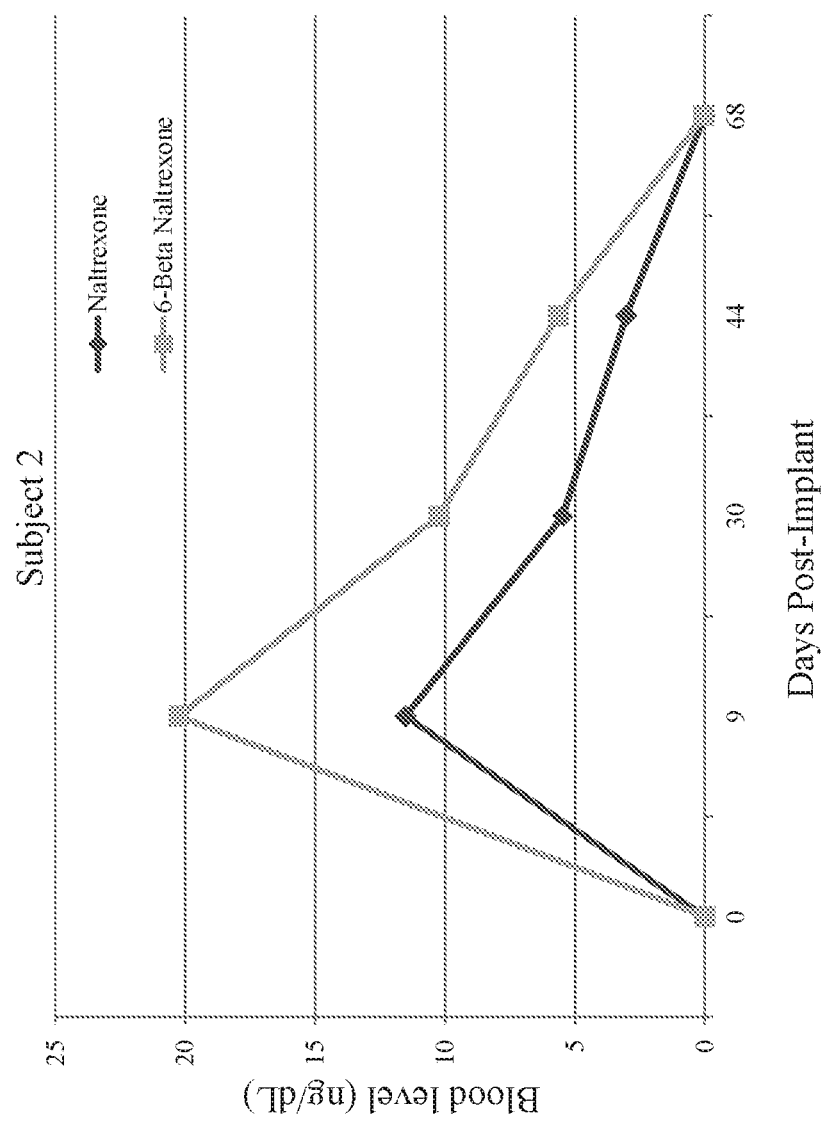
FIG. 3 shows naltrexone and 6-beta naltrexone blood levels over time in a second human subject implanted with a naltrexone-containing pellet, according to some embodiments.

In this example, 200 mg naltrexone-containing pellets were prepared according to the method provided in Example 5. Each 200 mg pellet was subcutaneously implanted in one of two human subjects. Peripheral blood draws were taken from the subjects over a period of time. The resultant levels of naltrexone and 6-beta naltrexone (the active metabolite of naltrexone) in heparanized blood are depicted in Table 6 and are also plotted in FIGS. 2 (levels for Subject 1) and 3 (levels for Subject 2). These data show that upon implantation, the naltrexone-containing pellets disclosed herein erode properly over time and are suitable to provide a therapeutically effective amount of naltrexone to the subjects.

TABLE 6

Implantation of 200 mg Naltrexone-Containing Pellets

|  | Days post-implant | Naltrexone (ng/dL) | 6-Beta Naltrexone (ng/dL) |
|---|---|---|---|
| Subject 1 | 15 | 5.15 | 8.23 |
|  | 22 | 4.98 | 6.85 |
|  | 29 | 5.31 | 8.74 |
|  | 43 | 3.74 | 3.32 |
|  | 57 | 3.28 | 4.44 |
|  | 71 | 3.29 | 6.15 |
|  | 93 | 0 | 0 |
| Subject 2 | 9 | 11.52 | 20.25 |
|  | 30 | 5.47 | 10.23 |
|  | 44 | 3.03 | 5.65 |
|  | 68 | 0 | 0.05 |

Example 12: Implantation of 100 mg Tadalafil-Containing Pellets

In this example, 100 mg tadalafil-containing pellets were prepared according to the method provided in Example 8. Each 100 mg pellet was subcutaneously implanted in one of two human subjects. Peripheral blood draws were taken from the subjects over a period of time. The resultant levels of tadalafil in heparanized blood are depicted in Table 7. These data show that upon implantation and after multiple weeks, tadalafil-containing pellets immediately provide tadalafil at therapeutically effective levels.

TABLE 7

Implantation of 100 mg Tadalafil -Containing Pellets

|  | Days post-implant | Tadalafil (ng/mL) |
|---|---|---|
| Subject 1 | 1 | 267.89 |
|  | 29 | 190.06 |
| Subject 2 | 8 | 245.36 |
|  | 29 | 235.67 |

Finally, it should be noted that there are alternative ways of implementing the embodiments disclosed herein. Accordingly, the present embodiments are to be considered as illustrative and not restrictive, and the claims are not to be limited to the details given herein, but may be modified within the scope and equivalents thereof.

The invention claimed is:

1. A pharmaceutical composition, comprising:
   76.8-86.8% of naltrexone;
   3-6% of stearic acid;
   10-20% of a pharmaceutically acceptable vehicle, wherein the vehicle is selected from glyceryl monostearate, glyceryl behenate, and glyceryl palmitostearate; and
   0.2% of ascorbic acid as a binder;
   wherein the pharmaceutical composition is a subcutaneously implantable pellet.

2. The pharmaceutical composition of claim 1, wherein the amount of naltrexone in the composition is 200 mg to 2,000 mg.

3. The pharmaceutical composition of claim 1, wherein the vehicle is glyceryl monostearate (GMS).

4. The pharmaceutical composition of claim 1, wherein the composition is formulated to erode in at least 90 days.

5. The pharmaceutical composition of claim 1, wherein the composition further comprises <1% of one or more antioxidants independently selected from methyl paraben and salts thereof, propyl paraben and salts thereof, vitamin E, α-Tocopherol polyethylene glycol succinate (Vitamin E TPGS), propyl gallate, sulfites, sodium benzoate, citric acid, cyclodextrins, peroxide scavengers, benzoic acid, ethylenediaminetetraacetic acid (EDTA) and salts thereof, chain terminators, butylated hydroxytoluene (BHT), butylated hydroxyanisole (BHA), and combinations thereof.

6. The pharmaceutical composition of claim 1, wherein the composition is formulated to deliver a therapeutically effective amount of the naltrexone over a period of time selected from the group consisting of 60 days, 80 days, 90 days, 100 days, 180 days, 6 months, 9 months, and 10 months.

7. The pharmaceutical composition of claim 6, wherein the therapeutically effective amount is from 1 ng/mL to 2 ng/mL and the period of time is 60 days.

8. A method of treating an addiction, selected from an opioid addiction, an alcohol addiction, and an amphetamine addiction, comprising administering the pharmaceutical composition of claim 1 to a subject.

\* \* \* \* \*

UNITED STATES PATENT AND TRADEMARK OFFICE
CERTIFICATE OF CORRECTION

PATENT NO. : 11,185,540 B2
APPLICATION NO. : 16/604506
DATED : November 30, 2021
INVENTOR(S) : Michael Anthony Pavlovich It is certified that error appears in the above-identified patent and that said Letters Patent is hereby corrected as shown below:

On the Title Page

Under "Related U.S. Application Data", please remove "(63) Provisional application No. 62/612,129, filed on Dec. 29, 2019" and correct item (60) as follows:
-- (60) Provisional application No. 62/484,769, filed on Apr. 12, 2017, Provisional application No. 62/612,129, filed on Dec. 29, 2019. --

Signed and Sealed this
Seventeenth Day of May, 2022

*Katherine Kelly Vidal*

Katherine Kelly Vidal
*Director of the United States Patent and Trademark Office*